United States Patent
Uchiyama et al.

(10) Patent No.: US 8,195,276 B2
(45) Date of Patent: Jun. 5, 2012

(54) IN-VIVO INFORMATION ACQUISITION APPARATUS AND IN-VIVO INFORMATION ACQUISITION APPARATUS SYSTEM

(75) Inventors: Akio Uchiyama, Kanagawa (JP); Hironobu Takizawa, Tokyo (JP); Ryo Karasawa, Tokyo (JP)

(73) Assignee: Olympus Corporation, Tokyo (JP)

( * ) Notice: Subject to any disclaimer, the term of this patent is extended or adjusted under 35 U.S.C. 154(b) by 220 days.

(21) Appl. No.: 10/564,303

(22) PCT Filed: Mar. 24, 2005

(86) PCT No.: PCT/JP2005/006201
§ 371 (c)(1),
(2), (4) Date: Jan. 10, 2006

(87) PCT Pub. No.: WO2005/092189
PCT Pub. Date: Oct. 6, 2005

(65) Prior Publication Data
US 2007/0106175 A1    May 10, 2007

(30) Foreign Application Priority Data

Mar. 25, 2004 (JP) ................................ 2004-090614
Mar. 25, 2004 (JP) ................................ 2004-090615

(51) Int. Cl.
*A61B 5/05*    (2006.01)

(52) U.S. Cl. ...................... 600/424; 600/564; 604/890.1

(58) Field of Classification Search .................. 600/562, 600/101, 564, 109, 424; 424/10.1; 348/56; 604/890.1
See application file for complete search history.

(56) References Cited

U.S. PATENT DOCUMENTS 5,279,607 A * 1/1994 Schentag et al. ........... 604/890.1
5,395,366 A * 3/1995 D'Andrea et al. ......... 604/890.1
(Continued)

FOREIGN PATENT DOCUMENTS
CN    2603657 Y    2/2004
(Continued)

OTHER PUBLICATIONS

Gavignet I., "Navette Intestinale Radiomettrice", Annales Francaises De Chronometrie Et De Microtecnhique, Observatoire De Besancon, Besancon, FR, vol. 47, 1998, pp. 91-94, XP000830917, ISSN, 0294-1228.

(Continued)

*Primary Examiner* — Max Hindenburg
*Assistant Examiner* — Renee Danega
(74) *Attorney, Agent, or Firm* — Scully, Scott, Murphy & Presser, P.C.

(57) ABSTRACT

There is provided an in-vivo information acquisition apparatus capable of detecting high-accuracy in-vivo information substantially at the same time in a plurality of different examination sites in a body cavity and an in-vivo information acquisition apparatus system capable of introducing a plurality of in-vivo information acquisition apparatuses into a patient at the same time. The in-vivo information acquisition apparatus includes a specimen-collecting section for collecting a specimen at an examination site in a body cavity, a specimen-evaluating section for evaluating the specimen collected by the specimen-collecting section and outputting an evaluation result, a labeling section having identification information unique to the in-vivo information acquisition apparatus, a communication section for receiving a signal transmitted from the outside and for transmitting to the outside the evaluation result output by the specimen-evaluating section, and a power supply section for supplying electrical power.

18 Claims, 20 Drawing Sheets

U.S. PATENT DOCUMENTS

| | | | |
|---|---|---|---|
| 6,240,312 B1 * | 5/2001 | Alfano et al. | 600/476 |
| 6,463,773 B1 | 10/2002 | Dimig | |
| 6,632,175 B1 * | 10/2003 | Marshall | 600/309 |
| 6,695,885 B2 * | 2/2004 | Schulman et al. | 623/25 |
| 7,063,671 B2 * | 6/2006 | Couvillon, Jr. | 600/562 |
| 7,141,016 B2 | 11/2006 | Lykke et al. | |
| 7,378,056 B2 * | 5/2008 | Black | 422/82.05 |
| 2001/0051766 A1 * | 12/2001 | Gazdzinski | 600/309 |
| 2002/0042562 A1 * | 4/2002 | Meron et al. | 600/361 |
| 2002/0111544 A1 * | 8/2002 | Iddan | 600/310 |
| 2002/0132226 A1 * | 9/2002 | Nair et al. | 435/4 |
| 2003/0020810 A1 | 1/2003 | Takizawa et al. | |
| 2003/0085994 A1 * | 5/2003 | Fujita et al. | 348/77 |
| 2003/0213495 A1 | 11/2003 | Fujita et al. | |
| 2004/0011366 A1 | 1/2004 | Schulman et al. | |
| 2005/0148842 A1 * | 7/2005 | Wang et al. | 600/407 |
| 2005/0149000 A1 | 7/2005 | Santini et al. | |

FOREIGN PATENT DOCUMENTS

| | | |
|---|---|---|
| FR | 2 843 872 | 3/2004 |
| GB | 2 374 149 A | 10/2002 |
| JP | 5-200015 | 8/1993 |
| JP | 2003-135388 | 5/2003 |
| WO | WO 99/32028 | 7/1999 |

OTHER PUBLICATIONS

U.S. Office Action dated Apr. 2, 2012, received in related U.S. Appl. No. 12/026,103.

* cited by examiner

IN-VIVO INFORMATION ACQUISITION APPARATUS AND IN-VIVO INFORMATION ACQUISITION APPARATUS SYSTEM

TECHNICAL FIELD

The present invention relates to in-vivo information acquisition apparatuses to be inserted into a body cavity to acquire in-vivo information and to in-vivo information acquisition apparatus systems.

Priority is claimed on Japanese Patent Application No. 2004-090614, filed Mar. 25, 2004, and Japanese Patent Application No. 2004-090615, filed Mar. 25, 2004, the contents of which are incorporated herein by reference.

BACKGROUND ART

An examination method using a capsule medical apparatus is known as a technique for checking the health condition of a subject (patient). According to this method, a subject swallows a medical device formed like a capsule to non-invasively examine for hematological or gastric disorders or other diseases in the body cavity with the medical device. This allows the health condition to be checked easily. Such a capsule medical apparatus is disclosed in, for example, Japanese Unexamined Patent Application Publication No. Hei-5-200015. Japanese Unexamined Patent Application Publication No. Hei-5-200015 discloses a medical capsule apparatus that includes an absorption channel for absorbing a body fluid into the capsule main body, a body-fluid collecting unit for collecting the body fluid absorbed into the capsule main body, a body-fluid testing unit for examining the collected body fluid, and a transmission unit for transmitting outside the body the examination result from the body-fluid testing unit.

This medical capsule apparatus (hereinafter, abbreviated just as the capsule) is advanced (or propelled) to an examination site in the body cavity and absorbs a body fluid into the capsule through the absorption channel by driving a micropump at the time of examination to detect the presence of blood in the body fluid using a blood sensor. When not carrying out examination, this blood sensor and the absorption channel are supplied with normal saline reserved in the capsule. This prevents a body fluid from being sensed by the blood sensor before the capsule reaches a predetermined examination site in the body cavity and increases the detection accuracy of in-vivo information when a plurality of sites are to be examined.

However, since the above-described capsule is constructed so as to detect in-vivo information at different examination sites while moving in the body cavity, the known capsule needs to supply normal saline to wash all fluid channels in the capsule each time an examination is conducted at a different examination site. Furthermore, with the known capsule, it is not possible to examine a plurality of different sites in the body cavity substantially at the same time. For this reason, it is necessary to insert a plurality of capsules into the body cavity to examine a plurality of sites at the same time.

DISCLOSURE OF INVENTION

The present invention has been conceived in light of the above-described circumstances, and an object of the present invention is to provide an in-vivo information acquisition apparatus capable of detecting high-accuracy in-vivo information substantially at the same time in a plurality of different examination sites in a body cavity and an in-vivo information acquisition apparatus system capable of introducing a plurality of in-vivo information acquisition apparatuses into a patient at the same time.

In order to achieve the above-described object, the present invention provides the following features.

The present invention provides an in-vivo information acquisition apparatus including a specimen-collecting section for collecting a specimen at an examination site in a body cavity; a specimen-evaluating section for evaluating the specimen collected by the specimen-collecting section and outputting an evaluation result; a labeling section having identification information unique to the in-vivo information acquisition apparatus; a communication section for receiving a signal transmitted from outside and for transmitting to the outside the evaluation result output by the specimen-evaluating section; and a power supply section for supplying electrical power.

With the above-described structure, the in-vivo information acquisition apparatus introduced into the body cavity can evaluate a specimen such as a body fluid and transmit the output in-vivo information outside the body via the communication section. At this time, since the in-vivo information acquisition apparatus includes the labeling section, evaluation results transmitted from a plurality of in-vivo information acquisition apparatuses introduced into the body cavity can be identified outside the body. Furthermore, a signal for simultaneously starting reactions can be transmitted via the communication section from outside the body to a plurality of in-vivo information acquisition apparatuses introduced into the body cavity.

In the in-vivo information acquisition apparatus according to the above-described invention, it is preferable that the labeling section be a labeling tag for transmitting the identification information via wireless communication.

With the above-described structure, electromagnetic waves can be emitted from outside the body towards the body cavity and signals sent from the labeling tags provided in the irradiated in-vivo information acquisition apparatuses can be received outside the body to identify a plurality of in-vivo information acquisition apparatuses substantially at the same time outside the body in a non-contact manner.

Furthermore, in the in-vivo information acquisition apparatus according to the above-described invention, it is preferable that the in-vivo information acquisition apparatus include a power supply control section that controls the supply of power of the power supply section based on the signal when the communication section receives the signal transmitted from the outside.

With the above-described structure, since each component of the in-vivo information acquisition apparatus can be supplied with power by transmitting a signal from the outside only when it is necessary, the capacity of the power supply section can be decreased and the in-vivo information acquisition apparatus can be made compact.

Furthermore, in the in-vivo information acquisition apparatus according to the above-described invention, it is preferable that the specimen-evaluating section include a photodetector for measuring an optical change of the specimen due to a reaction between the specimen and another substance.

With the above-described structure, a specimen such as a body fluid can be evaluated by measuring a change in light transmittance or an optical change such as coloration, discoloration, luminescence, or fluorescence in the specimen.

In the in-vivo information acquisition apparatus according to the above-described invention, it is preferable that the specimen-evaluating section have one of a blood sensor for detecting the presence of blood, a protein sensor for detecting a particular protein, an enzyme sensor for detecting a particular enzyme, and a gene sensor for detecting a particular gene.

With the above-described structure, if a specimen such as a body fluid includes blood, the specimen-evaluating section can evaluate the presence of blood in the body fluid, the concentration of blood, etc. and output this evaluation result. In the same manner, if an enzyme, a protein, or a gene is included in the body fluid, the specimen-evaluating section can detect these examination substances from the specimen such as a body fluid.

In addition, the present invention provides an in-vivo information acquisition apparatus system including an in-vivo information acquisition apparatus for acquiring in-vivo information at an examination site in a body cavity; a capsule medical apparatus having a function for storing the in-vivo information acquisition apparatus and releasing the in-vivo information acquisition apparatus at the examination site; an external antenna arranged outside a body to transmit and receive a signal to and from the in-vivo information acquisition apparatus; an external apparatus that acquires a signal transmitted by the in-vivo information acquisition apparatus from the external antenna and has an identifying section for identifying the identification information possessed by a labeling section arranged inside the in-vivo information acquisition apparatus; and an external control section provided in the external apparatus to transmit a common control signal to a plurality of the in-vivo information acquisition apparatuses With the above-described structure, the in-vivo information acquisition apparatus can be transported until the capsule medical apparatus reaches the desired examination site after it has been inserted into the body cavity by storing the in-vivo information acquisition apparatus in the capsule medical apparatus. Furthermore, the evaluation result transmitted by the in-vivo information acquisition apparatus can be acquired outside the body as in-vivo information by receiving the evaluation result using the external antenna. Furthermore, the transmission sources of evaluation results transmitted from a plurality of in-vivo information acquisition apparatuses can be identified in a non-contact manner by acquiring in the external apparatus the identification information sent from the labeling sections in the in-vivo information acquisition apparatuses and by identifying these items of identification information using the identifying section.

In addition, the external control section included in the external apparatus transmits a common control signal to a plurality of in-vivo information acquisition apparatuses in the body cavity, and thereby the external control section can control the plurality of in-vivo information acquisition apparatuses simultaneously.

In the in-vivo information acquisition apparatus system according to the above-described invention, it is preferable that the capsule medical apparatus include a storage section for storing a plurality of the in-vivo information acquisition apparatuses; a release unit for releasing the in-vivo information acquisition apparatuses from the storage section to the outside; and a control section for controlling the release unit.

With the above-described structure, the in-vivo information acquisition apparatuses can be transported until the capsule medical apparatus reaches the desired examination site after it has been inserted into the body cavity. Furthermore, the capsule medical apparatus can release at least one in-vivo information acquisition apparatus stored in the storage section to the outside from the storage section at the examination site in the body cavity under control of the control unit.

In addition, in the in-vivo information acquisition apparatus system according to the above-described invention, it is preferable that the capsule medical apparatus include an adjustment mechanism for adjusting the number of in-vivo information acquisition apparatuses to be released.

With the above-described structure, the capsule medical apparatus can release a desired number of in-vivo information acquisition apparatuses from the storage section to the outside at the examination site in the body cavity.

Furthermore, in the in-vivo information acquisition apparatus system according to the above-described invention, it is preferable that the in-vivo information acquisition apparatus system include a position-detecting section provided in at least one of the capsule medical apparatus and the external apparatus to detect the location of the in-vivo information acquisition apparatus in a body, wherein the capsule medical apparatus releases the in-vivo information acquisition apparatus based on the location information of the capsule medical apparatus acquired by the position-detecting section.

With the above-described structure, since the location of the capsule medical apparatus can be detected by the position-detecting unit provided in at least one of the in-vivo information acquisition apparatus and the external apparatus, the location where the in-vivo information acquisition apparatus releases the capsule medical apparatus can be controlled. Furthermore, regions of lesions can be identified by combining information about the release position of the in-vivo information acquisition apparatus and the in-vivo information acquired by the in-vivo information acquisition apparatus.

According to the in-vivo information acquisition apparatus and the in-vivo information acquisition apparatus system of the present invention, in-vivo information such as a gastric disorder in a plurality of sites can be detected and acquired with high accuracy by introducing into the body cavity a plurality of in-vivo information acquisition apparatuses capable of detecting in-vivo information about a subject.

BEST MODE FOR CARRYING OUT THE INVENTION

First Embodiment

An in-vivo information acquisition apparatus system according to a first embodiment of the present invention will now be described with reference to FIGS. 1 to 9.

Figure 1:
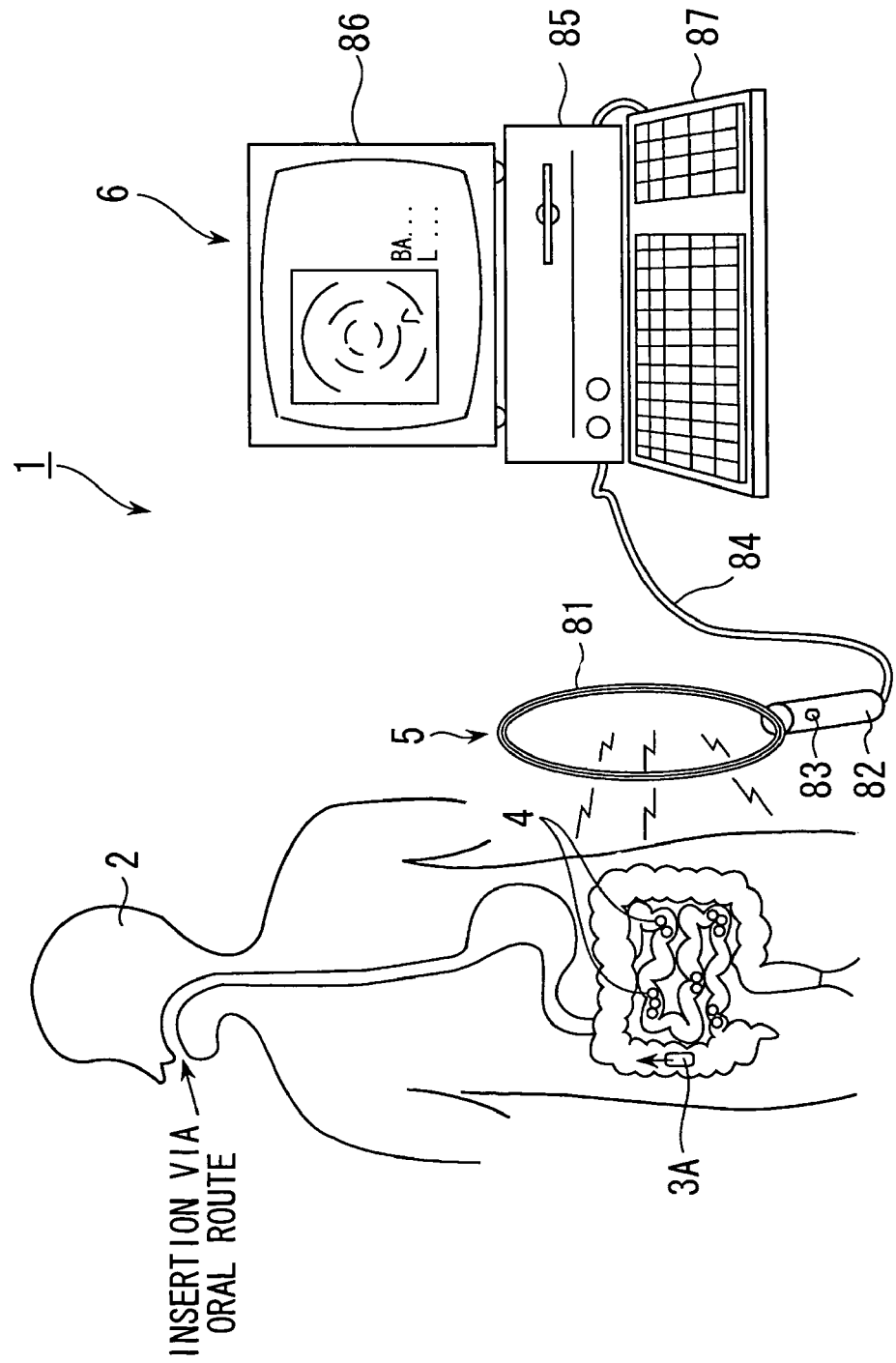
FIG. 1 is a schematic diagram depicting the overall structure of an in-vivo information acquisition apparatus system according to a first embodiment of the present invention.

Referring to FIG. 1, an in-vivo information acquisition apparatus system 1 includes a capsule medical apparatus 3A, detection cells 4 (in-vivo information acquisition apparatuses), an external antenna 5, and an external apparatus 6.

Here, as shown in FIG. 1, the capsule medical apparatus 3A storing a plurality of detection cells 4 (in-vivo information acquisition apparatuses) is inserted into the body cavity of the patient 2 per oral or per anal. The capsule medical apparatus 3A transports the detection cells 4 to examination sites and releases the detection cells 4 into the body cavity. Thereafter, the detection cells 4 (in-vivo information acquisition apparatuses) acquire in-vivo information from the examination sites in the body cavity and transmit the acquired information to outside the body. The detection cells 4 are each a compact examination apparatus for detecting blood (hemoglobin), tumor markers, protein, DNA, etc. included in a specimen such as a body fluid in an examination site in the body cavity and transmitting the acquired examination data outside the body using, for example, electromagnetic waves. The external antenna 5 transmits a signal for controlling each of the detection cells 4 and receives a signal indicating in-vivo information acquired from the detection cell 4. The external apparatus 6 is disposed outside the body of the patient 2, and controls the detection cells 4 via the external antenna 5, records acquired in-vivo information, and so on.

Figure 2:
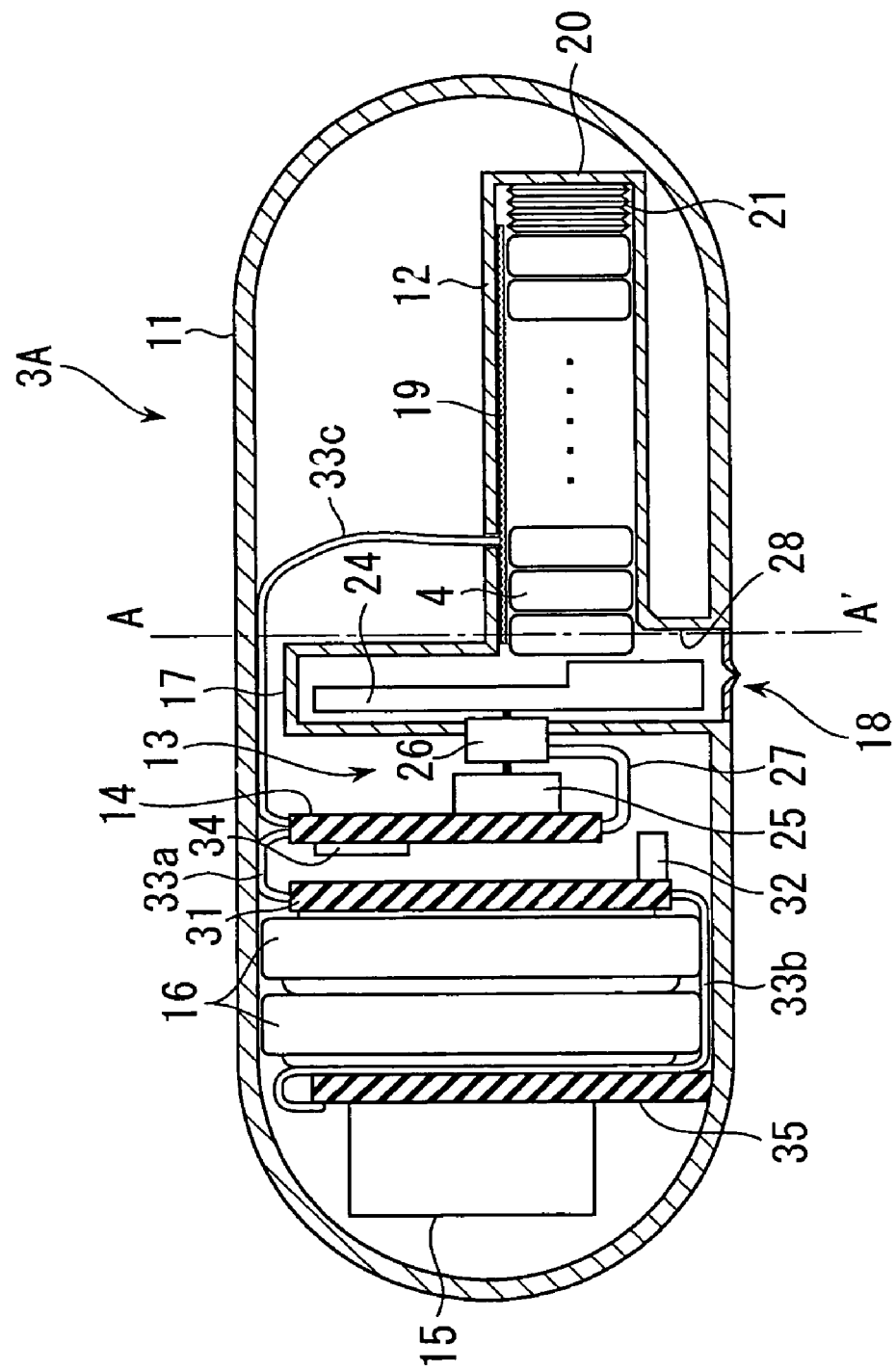
FIG. 2 is a diagram depicting the internal structure of a capsule medical apparatus in the in-vivo information acquisition apparatus system shown in FIG. 1.

As shown in FIG. 2, the capsule medical apparatus 3A has a casing 11 formed like a capsule made of synthetic resin such as polysulfone or polyurethane, and includes a storage container 12, a release unit 13, a control board (control section) 14, a timer 15, and batteries 16 in the casing 11.

The storage container 12 has an opening at one end and stores a plurality of the detection cells 4 arranged in a row. The release unit 13 has a mechanism for sequentially releasing the detection cells 4 through the opening of the storage container 12. The control board 14 includes a control circuit (not shown) for subjecting the internal components of the capsule medical apparatus 3A to electrical control processing, for example. The timer 15 is arranged at one end (left side) of the casing 11, and keeps time for releasing each of the detection cells 4 from the release unit 13. The batteries 16 are arranged between the timer 15 and the control board 14, and supply operating power to the internal electrical system of the capsule medical apparatus 3A.

As shown in FIG. 2, a hollow, large-diameter cam container 17 is connected to the open end of the storage container 12. The cam container 17 includes the release unit 13 for pushing out the detection cells 4 stored in the storage container 12 via a release port 18 located substantially at the center of the outer circumferential surface of the casing 11. On the inner surface of the storage container 12, a metal electrode 19 (electrical connection) electrically connected to the detection cells 4 is provided from the open end to another end 20. This metal electrode 19 is electrically connected to the control board 14 by a flexible board 33c disposed in a hole provided at part of the storage container 12. At the other end 20 of the storage container 12 is provided an elastic member 21 for pushing the detection cells 4 towards the cam container 17.

The release unit 13 includes a substantially disc-shaped cam 24 arranged in the cam container 17, a motor 25 mounted on the control board 14, and a transmission gear 26 mounted on a wall surface of the cam container 17. The cam 24 includes a cutout 22 and a projection 23. In the cam container 17, the cam 24 delivers the detection cells 4 (4a, 4b, and so on) to the release port 18 one at a time. The operation of the motor 25 is controlled by a control signal from the control board 14 to rotate the cam 24. The transmission gear 26 is connected between the cam 24 and the motor 25 to control the rotational speed of the cam 24. The transmission gear 26 is electrically connected to the control board 14 via a flexible board 27, so that the rotational speed is controlled by a control signal from the control board 14.

The hollow interior of the cam container 17 defines a substantially cylindrical space with substantially the same inner diameter as the outer diameter of the cam 24. In the interior of the cam container 17, a release slot 28 is also formed between the storage container 12 and the release port 18 on the surface facing the cutout 22 and projection 23 of the cam 24. This release slot 28 guides the detection cells 4 to the release port 18 when the detection cells are released externally. The opening of the storage container 12 is located adjacent to the release port 18 of the casing 11 such that the storage container 12 and the cam container 17 are eccentric. For this reason, the detection cells 4 travel only a short way when the detection cells 4 are released externally.

Figure 3A:
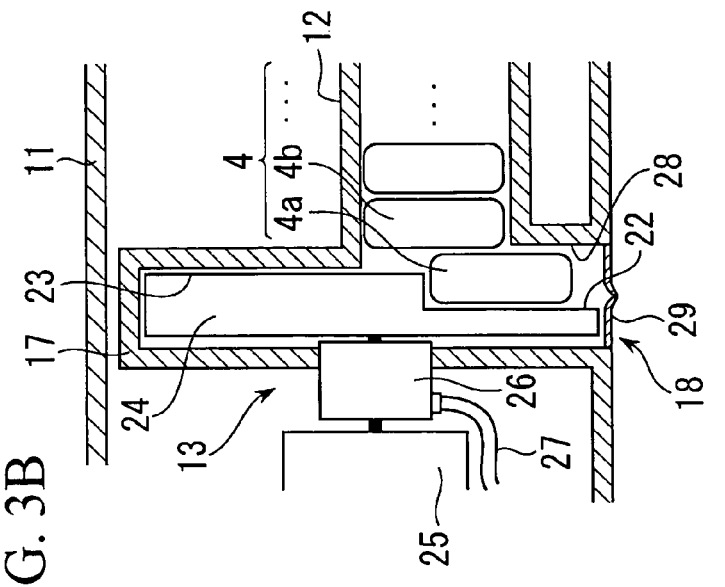
FIG. 3 includes side elevational views of a release unit of the capsule medical apparatus shown in FIG. 2.
Figure 3B:
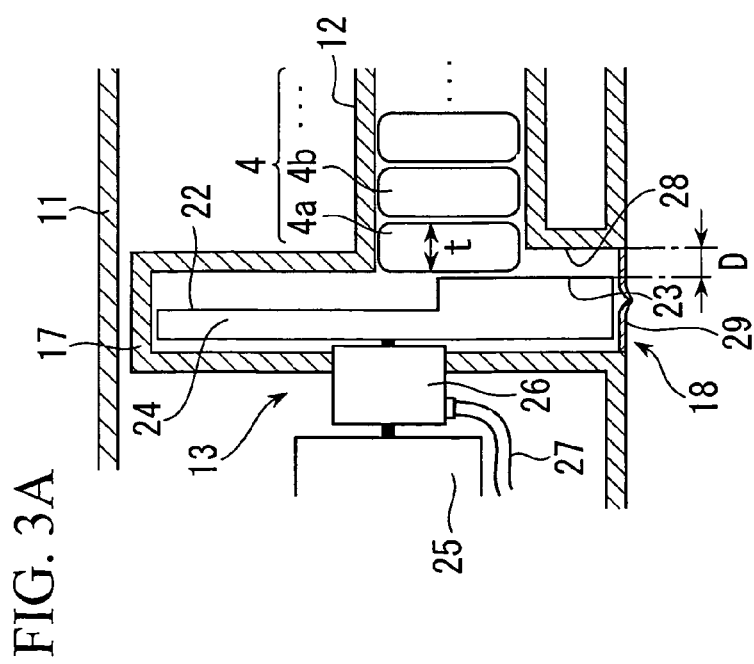
Figure 3C:
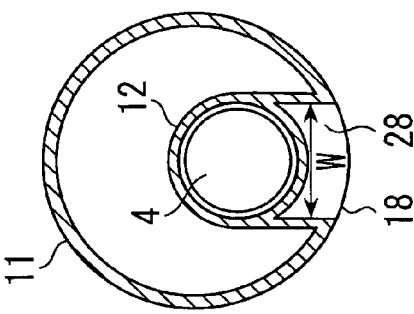
Figure 4A:
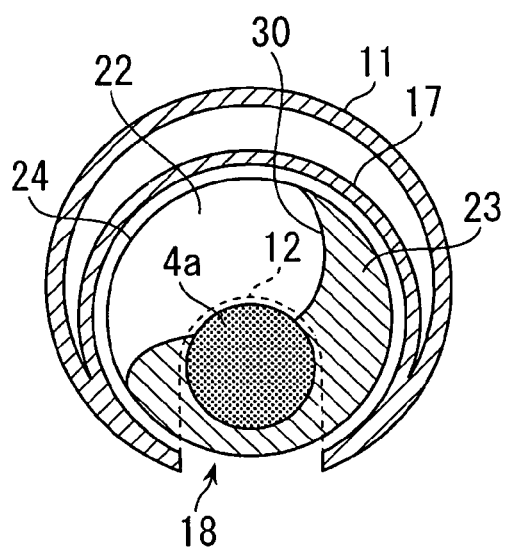
FIG. 4 includes front elevational views illustrating the operation of a cam when a detection cell is released.
Figure 4B:
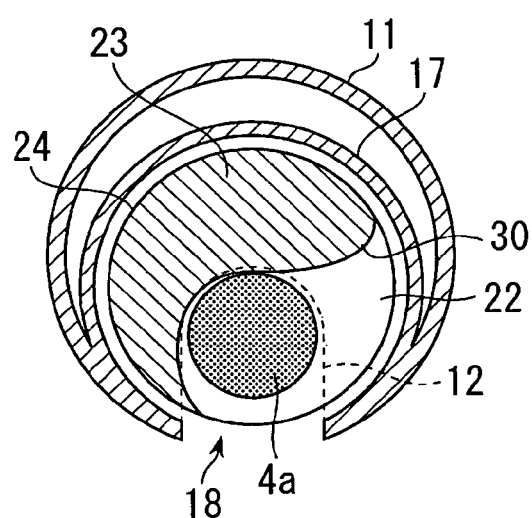
Figure 4C:
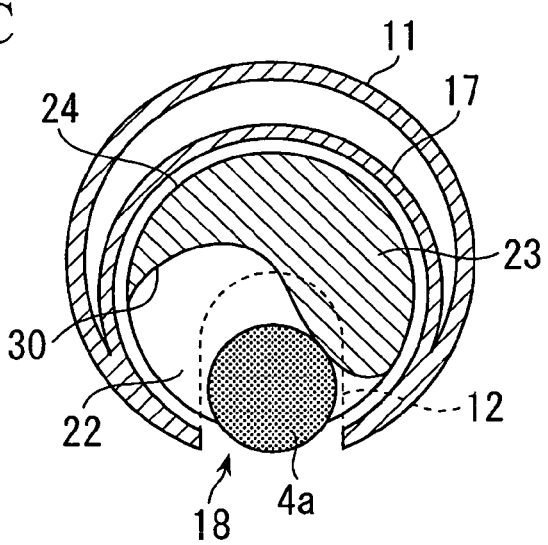

FIGS. 3A to 3C are magnified cross-sectional views including the release unit 13. FIGS. 3A and 3B are longitudinal cross-sectional views of the capsule medical apparatus 3A, and FIG. 3C is a cross-sectional view taken along line A-A' of the capsule medical apparatus 3A shown in FIG. 2. FIGS. 4A to 4C are front elevational views of the cam 24 as viewed from the storage container 12, and illustrate the rotation of the cam 24 when the cam 24 releases a detection cell 4.

As shown in FIGS. 3A and 3C, when the cam 24 is rotated to cause the projection 23 to face the release slot 28, the distance D between the top surface of the projection 23 and the bottom surface of the release slot 28 is set to be smaller than the thickness t of each of the detection cells 4. The width W between the lateral surfaces of the release slot 28 is set to a value slightly larger than the external size of the detection cells 4. The release port 18 has a width equal to the width W of the release slot 28. This release port 18 is provided with a check valve 29 for preventing a body fluid from flowing into the casing 11 and preventing the released detection cells 4 from coming back in. This check valve 29 includes a pair of elastic membranous members that are opened outward of the casing 11 when the detection cell 4 is to be released and are closed after the detection cell 4 has been released.

When the projection 23 faces the release slot 28, as shown in FIG. 3A, the top surface of the projection 23 prevents the detection cell 4a from moving toward the release slot 28, and hence the detection cell 4a remains in the storage container 12. When the cutout 22 faces the release slot 28, as shown in FIG. 3B, the gap between the top surface of the cutout 22 and the bottom surface of the release slot 28 is slightly larger than the thickness t of the detection cell 4. Therefore, the detection cell 4a is capable of moving towards the cutout 22 by the pressing force of the elastic member 21, and proceeds to the release slot 28.

As shown in FIG. 4, a cam surface 30 formed along the boundary between the projection 23 and the cutout 22 of the cam 24 exhibits a gentle S-shaped curve. FIG. 4A shows the detection cell 4a remaining in the storage container when the projection 23 faces the release slot 28. FIG. 4B shows the detection cell 4a guided by the cutout 22 when the cutout 22 faces the release slot 28. FIG. 4C shows the cam surface 30 pushing the detection cell 4a towards the release port 18. This state is achieved when the cam 24 in FIG. 4B is rotated.

More specifically, in a normal state where the detection cell 4 is stored in the storage container 12, the projection 23 faces the release slot 28 to prevent the detection cell 4 from moving to the release slot 28. On the other hand, when the detection cell 4 is to be released from the storage container 12 through the release port 18, the motor 25 is driven to rotate the cam 24 so that the cutout 22 faces the release slot 28. In this manner, the detection cell 4 is guided into the cutout 22 to cause the cam surface 30 to push the detection cell 4a accommodated in the cutout 22 towards the release port 18.

In a state immediately after the detection cell 4a has been released from the release port 18, the detection cell 4b to be released subsequently remains in the storage container 12 because part of the projection 23 of the cam 24 faces the release slot 28. After the cam 24 has rotated by one rotation, the detection cell 4b is guided into the cutout 22 of the cam 24 by the pressing force of the elastic member 21. The detection cell 4b guided by the cutout 22 is pushed towards the release port 28 in the same manner as the detection cell 4a is released. Through the above-described series of operations, the plurality of detection cells 4 are released from the storage container 12 one detection cell 4 at a time.

As shown in FIG. 2, the two batteries 16 are, for example, button-shaped. They are used as built-in power supply units of the capsule medical apparatus 3A. The batteries 16 are arranged so as to be stacked one on the other along the axial direction of the casing 11 to electrically connect to a power supply board 31. The power supply board 31 is connected to the control board 14 via a flexible board 33a, so that the operating power of the batteries 16 is fed to the circuit for each component. The power supply board 31 is provided with an internal switch 32 formed of, for example, a bias magnet and a reed switch to turn ON/OFF the operating power supplied from the batteries 16.

The timer 15 is fixed to a timer board 35 connected to the control board 14 via a flexible board 33b. The timer 15 starts measuring time with a control signal from the control board 14 to send time information to the control board 14 via the flexible board 33b.

The control board 14 is also provided with a memory 34. The memory 34 pre-stores time information to operate the release unit 13 when releasing the detection cells 4 and information regarding the number of released detection cells 4 in examination sites. The number of released detection cells 4 stored in the memory 34 can be any value, depending on the substances to be detected in the body cavity and the purposes of examination. For example, when the main purpose is to examine for intestinal disorders, many detection cells 4 are released in the intestine, whereas few detection cells 4 are released in sites other than the intestine, such as the colon. Furthermore, the same number of detection cells 4 may be released in all examination sites.

On the control board 14, all circuits including the flexible boards 33a and 33b are electrically connected. Through the control board 14, it is possible to supply operating power from the batteries 16 via the power supply board 31 and to control the circuits for various components, including the motor 25, the transmission gear 26, and the memory 34. For example, the control board 14 can read time information from the timer 15, as well as information about the release times of the detection cells 4 and the number of released detection cells 4 from the memory 34 to process these items of information. Thereafter, the control board 14 can send an operational signal to the motor 25 and the transmission gear 26 at predetermined times stored in the memory 34, thereby exercising control so as to release the required number of detection cells 4 from the casing 11 at the predetermined times.

Figure 5A:
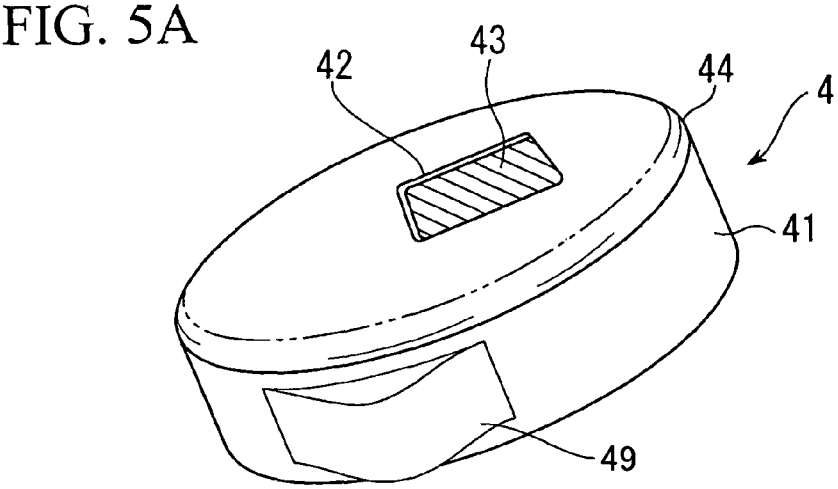
FIG. 5 includes schematic diagrams depicting the external appearance of a detection cell in the in-vivo information acquisition apparatus system shown in FIG. 1.
Figure 5B:
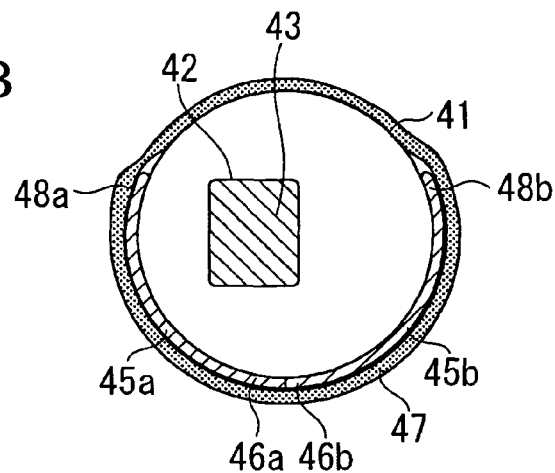
Figure 5C:
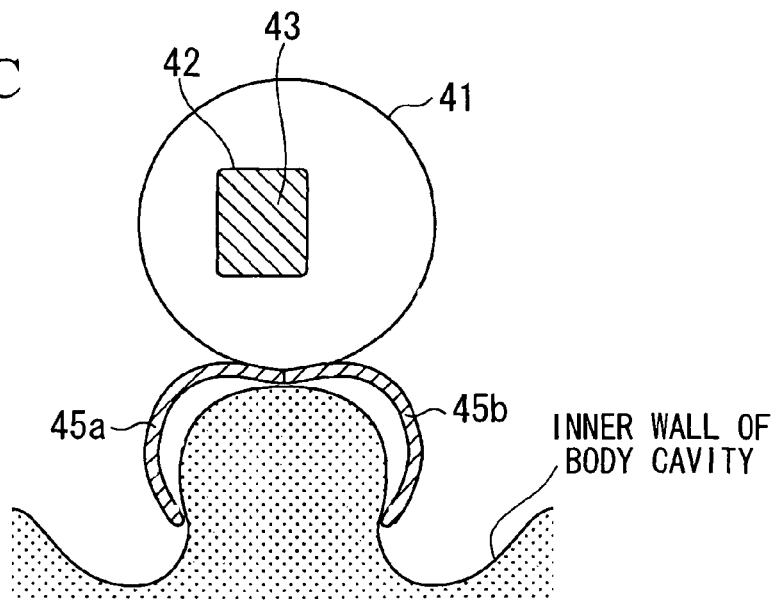

FIG. 5 includes diagrams depicting the external appearance of the detection cell 4. FIG. 5A is a perspective view of the detection cell 4, and FIGS. 5B and C are front elevational views of the detection cell 4. FIG. 5B shows a state before the detection cell 4 is indwelled in the body cavity. In FIG. 5C, the detection cell 4 is indwelled in the body cavity.

As shown in FIG. 5A, the detection cell 4 is formed to be hermetically sealed with a cell enclosure 41 made of synthetic resin, such as polysulfone and polyurethane. This cell enclosure 41 is a compact disc shape, for example, 3 mm in diameter and 0.5 mm in thickness, so that the capsule medical apparatus 3A can contain a plurality of detection cells 4 in the storage container 12. The cell enclosure 41 has on its surface a substantially rectangular sampling port (specimen-collecting section) 42 for pulling in a specimen such as a body fluid and a shutter 43 provided so as to close the sampling port 42 from inside the cell enclosure 41. A rim 44 of the cell enclosure 41 is round so that the detection cell 4 can be released smoothly from the capsule medical apparatus 3A.

In addition, as shown in FIGS. 5B and C, the cell enclosure 41 has leaf springs (indwelling sections) 45a and 45b mounted on its lateral surface. One set of ends 46a and 46b of the leaf springs 45a and 45b are fixed side-by-side with screws or adhesives on the lateral surface of the cell enclosure 41. A soluble flexible membrane 47, such as a wafer, is also provided so as to cover the leaf springs 45a and 45b. The soluble flexible membrane 47 is bonded to the other set of ends 48a and 48b of the leaf springs 45a and 45b with adhesives. It is noted that in FIG. 5A the indwelling section is not shown for the sake of convenience. FIGS. 5B and 5C show a state in which the soluble flexible membrane 47 covers the entire lateral surface of the cell enclosure 41. The present invention is not limited to this example, however. The soluble flexible membrane 47 may cover only part of the lateral surface of the cell enclosure 41 and expose the other part of the cell enclosure 41. A conductive rubber member 49 in contact with the metal electrode 19 on the storage container 12 of the above-described capsule medical apparatus 3A may be provided on this exposed part of the lateral surface of the cell enclosure 41. This conductive rubber member 49 has a smooth convex shape so as to ensure reliable connection to the metal electrode 19 provided on the inner surface of the storage container 12.

While the detection cell 4 is stored in the storage container 12 of the capsule medical apparatus 3A, the leaf springs 45a and 45b are fixed to the lateral surface of the detection cell 4 with the soluble flexible membrane 47. When the detection cell 4 is released from the capsule medical apparatus 3A into the body cavity, the soluble flexible membrane 47 fixed to the leaf springs 45a and 45b is dissolved by the body fluid in the body cavity. At this time, as shown in FIG. 5C, the leaf springs 45a and 45b pinch the inner wall of the body cavity by their own elastic force. Although a wafer is used as the soluble flexible membrane 47 in the above-described structure, any substance that is readily dissolved in a liquid containing water is acceptable as the soluble flexible membrane 47. Furthermore, any member having elastic force may be used instead of the leaf springs 45a and 45b.

Figure 6A:
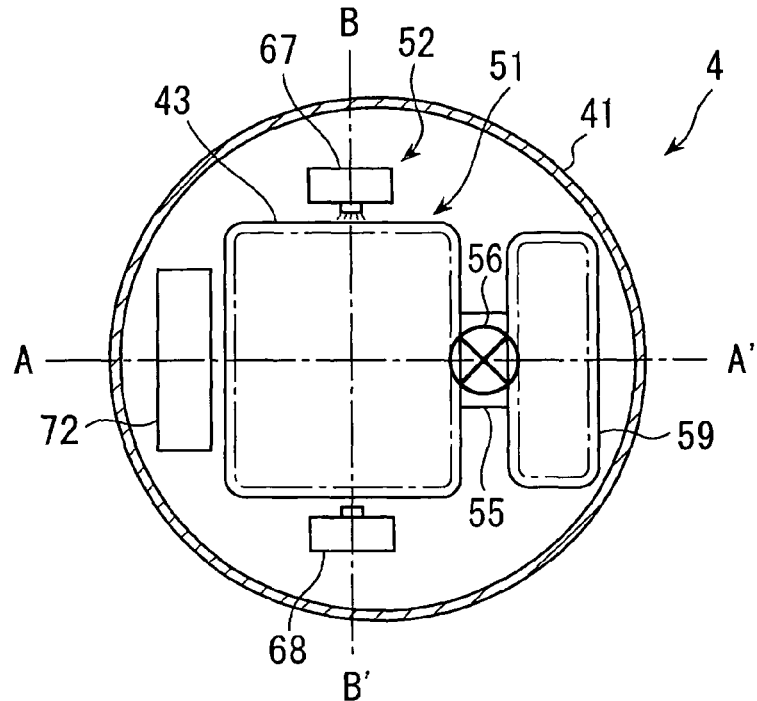
FIG. 6 includes diagrams depicting the internal structure of the detection cell shown in FIG. 5.
Figure 6B:
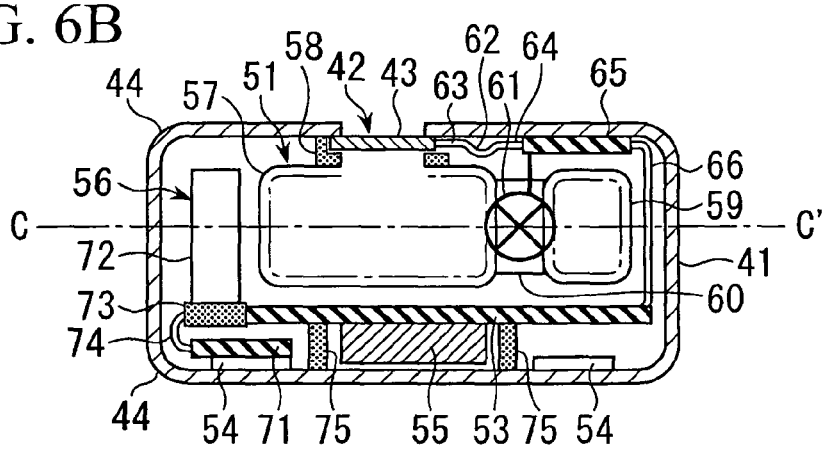
Figure 6C:
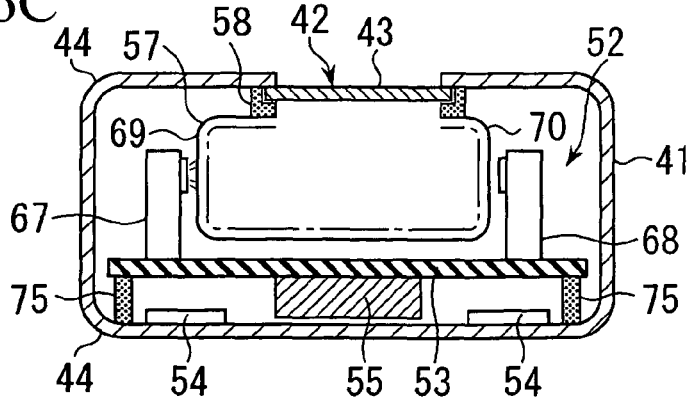

FIG. 6 includes cross-sectional views of parts of the detection cell 4. FIG. 6A is a cross-sectional view of the detection cell 4, FIG. 6B is a cross-sectional view taken along line A-A' of the detection cell 4 shown in FIG. 6A, and FIG. 6C is a cross-sectional view taken along line B-B' of the detection cell 4 shown in FIG. 6A. FIG. 6A corresponds to a cross-sectional view taken along line C-C' shown in FIG. 6B.

As shown in FIG. 6, the detection cell 4 has the disc-shaped cell enclosure 41. The detection cell 4 further includes in the cell enclosure 41 a reaction unit 51, a reaction-detecting section (specimen-evaluating section) 52, a signal processing board 53, an intracellular antenna (communication section) 54, a memory 55, and a power supply (power supply section) 56.

The reaction unit 51 includes a reactor tank 57 in which a specimen, such as a body fluid, collected from the body cavity reacts with another substance. Furthermore, the reaction-detecting section 52 is arranged near the reaction unit 51 to detect the reaction result of the specimen in the reaction unit 51. The signal processing board 53 includes a signal processing circuit for subjecting the internal components of the detection cell 4 to control processing and for processing the reaction result from the reaction-detecting section 52. The intracellular antenna 54 is arranged below the signal processing board 53 to transmit/receive a signal for controlling the detection cell 4, a signal such as in-vivo information, and other signals to/from the external antenna 5. The memory 55 (labeling section) is mounted on the bottom surface of the signal processing board 53 to store in-vivo information acquired in the reaction-detecting section 52, setting information such as a reaction condition when the external apparatus 6 conducts an examination, and an identification code unique to each detection cell. The power supply 56 is mounted on the top surface of the signal processing board 53 to supply operating power to the electrical system in the detection cell 4.

As shown in FIG. 6, the reaction unit 51 includes the reactor tank 57, an absorption channel 58, a reagent container 59, and a micropump 61. The reactor tank 57 is connected to the sampling port 42 via the absorption channel 58 to cause a specimen, such as a body fluid, collected from the sampling port 42 to react with another substance. The reagent container 59 stores an antibody or a labeling reagent that specifically reacts with an antigen such as a tumor marker antigen or a blood component antigen included in the collected specimen. The micropump 61 absorbs an antibody or a reagent (hereinafter, abbreviated as a substance such as an antibody) from the reagent container 59 into the reactor tank 57 via a reagent supply channel 60.

The reactor tank 57 is made of synthetic resin with high optical transparency, such as polycarbonate, cyclo olefin polymer, or PMMA (polymethylmethacrylate). The pressure in the reactor tank 57 is maintained to be lower than that in the body cavity, so that a specimen such as a body fluid flows into the reactor tank 57 from the sampling port 42 the moment the shutter 43 is opened.

One end of the shutter 43 is connected to, for example, one end 63 of an ion-conducting actuator 62, and the other end 64 of the ion-conducting actuator 62 is fixed to a drive board 65. The ion-conducting actuator 62 exhibits distortion when a voltage is applied thereto. Based on this characteristic, the shutter 43 connected to the end 63 can be slid open when a voltage is applied while the other end 64 is fixed to the cell enclosure 41. The micropump 61 is fixed to the drive board 65, which is connected to the signal processing board 53 with a driving flexible board 66. In short, the micropump 61 and the ion-conducting actuator 62 are operated by a control signal sent to the drive board 65 from the signal processing board 53.

When a reaction between the collected specimen and a substance such as an antibody is to be started, a voltage is applied to the ion-conducting actuator 62 to open the shutter 43, which introduces into the reactor tank 57 a specimen such as a body fluid in the body cavity from the sampling port 42. Thereafter, the micropump 61 is operated by a control signal from the driving circuit of the drive board 65 to absorb the substance such as an antibody stored in the reagent container 59 into the reactor tank 57.

As shown in FIG. 6, the reaction-detecting section 52 includes an illuminating element 67 and a photodetector 68 provided on the signal processing board 53 such that the reactor tank 57 is disposed between the illuminating element 67 and the photodetector 68. The illuminating element 67 is realized by, for example, a white LED. It is arranged so as to face one surface 69 of the reactor tank 57 to illuminate the reactor tank 57 with illuminating light. The photodetector 68 is realized by, for example a PIN photodiode. It is arranged so as to face another surface 70 of the reactor tank 57 on the optical axis of the illuminating element 67 to detect light that passes through the reactor tank 57. An LED driving circuit (not shown) is electrically connected to the illuminating element 67 for driving the light-emitting section of the illuminating element 67 to intermittently fire a flash of light.

Before starting a reaction between the collected specimen and the substance such as an antibody, the illuminating element 67 emits illuminating light onto the reactor tank 57 with no specimen such as a body fluid in the reactor tank 57. The light that has passed through the reactor tank 57 is received at the photodetector 68 as a reference beam. The reference beam received at the photodetector 68 is converted into an electrical current signal corresponding to the light intensity and sent to the signal processing board 53 for temporary storage in the memory 55. Data of the reference beam stored in this memory 55 is used as reference data.

Next, during or after a reaction of the specimen with the substance such as an antibody in the reactor tank 57, the illuminating element 67 again emits illuminating light onto the reactor tank 57 filled with the reaction substance. Light that has passed through the reactor tank 57 is received at the photodetector 68 as measuring light. Measuring light acquired in the photodetector 68 is converted into an electrical current signal according to the light intensity, as described above, is sent to the signal processing board 53, and is stored in the memory 55 as measurement data. The measurement data and reference data stored in the memory 55 are subjected to an arithmetic operation, such as subtraction, in the signal processing circuit of the signal processing board 53. The evaluation result output through this arithmetic operation is stored again in the memory 55 as examination data.

The intracellular antenna 54 is electrically connected to a communication board 71. The communication board 71 is provided with a communication circuit for selectively extracting an electromagnetic wave coming from the external antenna 5, received with the intracellular antenna 54, for wave detection, demodulating a control signal from the external apparatus 6, and outputting the demodulated signal to, for example, the circuit for each component. Furthermore, the communication circuit has a function for modulating signals such as examination data and an identification code based on a carrier wave with a predetermined frequency, and transmitting electromagnetic waves to the external antenna 5 as in-vivo information from the intracellular antenna 54.

In addition to the function for storing measurement data and reference data, the memory 55 has functions for saving an identification code unique to each detection cell and storing a communication protocol to control when a signal is to be transmitted externally from the intracellular antenna 54. The memory 55 has a function for saving a computation program for applying arithmetic operations to the measurement data, reference data, etc. in the signal processing circuit on the signal processing board 53.

As shown in FIG. 6, the power supply 56 is realized by, for example, a storage battery 72 and supplies the internal electrical system in the detection cell 4 with operating power. This storage battery 72 is connected to the signal processing board 53 via a selection switch 73, and hence operating power of the storage battery 72 is fed to the circuit for each component via the signal processing board 53.

This selection switch 73 is connected to the conductive rubber member 49 (not shown in the figure) provided on the cell enclosure 41. More specifically, when the detection cell 4 is accommodated in the storage container 12 of the capsule medical apparatus 3A, electrical power supplied from the metal electrode 19 of the storage container 12 can be fed to the storage battery 72 via the conductive rubber member 49 and the selection switch 73.

Furthermore, a flexible board 74 for communication is connected between the selection switch 73 and the communication board 71 so that signals can be transmitted between the storage battery 72, the signal processing board 53, and the communication board 71. The storage battery 72 can be charged by, for example, the intracellular antenna 54 receiving an electromagnetic wave emitted from the external antenna 5 towards the body cavity and transmitting an electrical signal acquired as a result of the reception to the storage battery 72 via the flexible board 74 for communication. Switching between supplying power to the circuit for each component and charging through the intracellular antenna 54 or the conductive rubber member 49 is achieved with the selection switch 73.

The signal processing board 53 is fixed with a plurality of support posts 75 provided on the inner surface of the cell enclosure 41, and the circuits of components such as the driving flexible board 66 and the memory 55 are electrically connected. This signal processing board 53 has functions for supplying operating power from the power supply 56 to the drive board 65 through the driving flexible board 66, controlling the components in the detection cell 4, and processing acquired data. As described above, on the signal processing board 53, for example, measurement data and reference data acquired in the photodetector 68 are saved in the memory 55, and this data stored in the memory 55 is read for arithmetic operations, etc. Furthermore, the signal processing board 53 has a control function for issuing a command related to the transmission/reception of signals to/from the external antenna 5 via the intracellular antenna 54.

As shown in FIG. 1, the external antenna 5 disposed outside the body of the patient 2 includes a coil (not shown) wound in a loop in an annular member 81 and a capacitor (not shown) connected to an edge of the coil. A handle 82 is connected to the annular member 81, so that, for example, the operator can hold the handle 82 to position the external antenna 5 at any location outside the body. Although the annular member 81 is not limited to a particular size, it is preferable that the outer diameter of the annular member 81 be substantially equal to the body width of the patient 2. This ensures that in-vivo information is acquired from the detection cells 4 indwelled in the body cavity without having to move the external antenna 5 very frequently.

Furthermore, the handle 82 is provided with a switch 83 for turning ON/OFF the external antenna 5. A communication cable 84 for communication, such as a USB cable, is attachably/detachably connected to the handle 82. This external antenna 5 has functions for receiving electromagnetic waves transmitted from the detection cells 4 to transfer signals such as examination data and identification codes to the external apparatus 6 via the communication cable 84 and converting control signals sent from the external apparatus 6 into electromagnetic waves to transmit them to the detection cells 4.

As shown in FIG. 1, the external apparatus 6 is realized by, for example, a personal computer (hereinafter, abbreviated as PC) 85. The PC 85 includes an internal hard disk (not shown) that saves examination data transferred from the external antenna 5. Connected to the PC 85 are a display section 86 for displaying examination data saved in the hard disk during or after examination and a keyboard 87 as an example of an operating panel for entering data.

The PC 85 includes therein an identifying section for identifying an identification code transmitted from each of a plurality of detection cells 4. The identifying section identifies in a short time a plurality of detection cells 4 in a non-contact manner by analyzing identification codes received by the external antenna 5. Furthermore, the PC 85 includes an external control section (not shown in the figure) for transmitting a common control signal to the plurality of detection cells 4.

Figure 7:
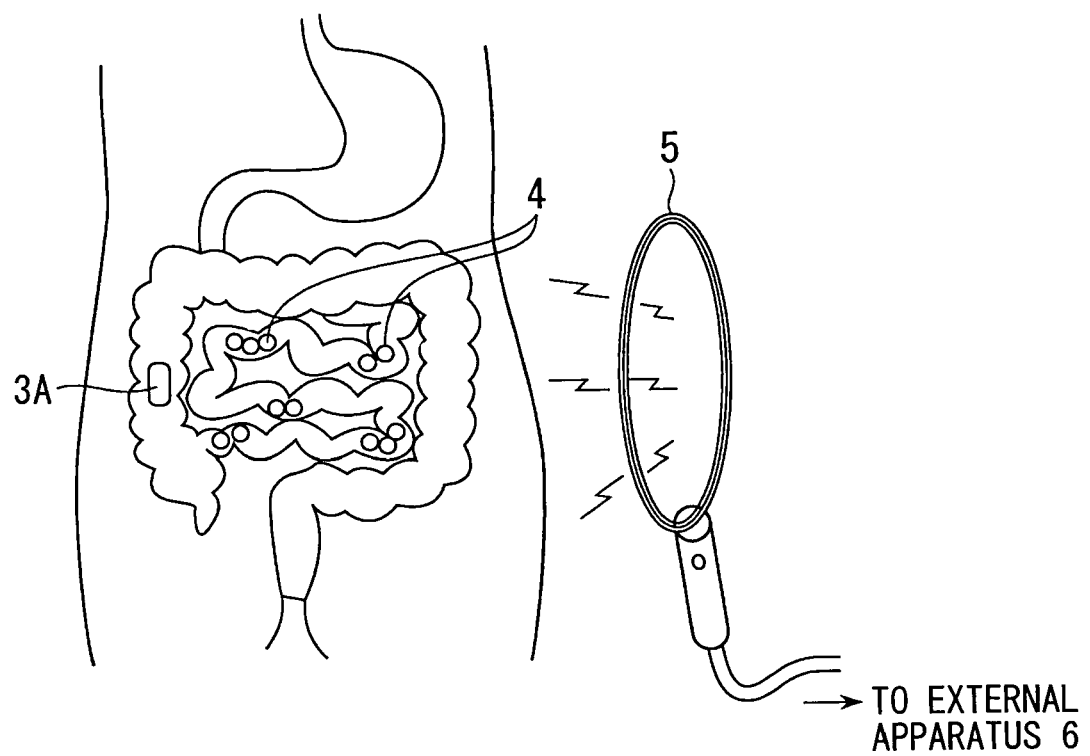
FIG. 7 is a diagram illustrating the read-out of in-vivo information from detection cells.

Referring to FIG. 7, when the external apparatus 6 reads out examination data from a plurality of detection cells 4, the patient 2, the physician, or the like positions the external antenna 5 at an extracorporeal location near the examination site and presses, for example, the switch 83 to emit from the external antenna 5 a command signal for reading out in-vivo information over a wide region in the body by using electromagnetic waves. The command signal includes a code equivalent or corresponding to the identification code of the detection cell 4 from which examination data is to be read. A plurality of detection cells 4 existing in the radiation area of the electromagnetic waves receive the command signal with their respective intracellular antennas 54 and send it as electrical signals to the signal processing boards 53 via the communication boards 71. At this time, each of the signal processing boards 53 reads out the identification code and examination data stored in the memory 55, and, if the code of the command signal matches the identification code read from the memory 55, sends them to the communication board 71 according to a communication protocol. The identification code and examination data sent to the communication board 71 are transmitted externally from the intracellular antenna 54 as electromagnetic waves.

Outside the body cavity, the external antenna 5 receives a signal including the examination data transmitted from the detection cell 4 in the body cavity. The external apparatus 6 saves the examination data transferred from the external antenna 5 in, for example, the hard disk of the PC 85.

Before the capsule medical apparatus 3A is introduced into the patient 2, data indicating release times of the detection cells 4 set in the timer 15 of the capsule medical apparatus 3A is saved in the hard disk of the PC 85 constituting the external apparatus 6.

The operation according to this embodiment will now be described.

Before an examination of the patient 2 is started, the technician or the operator turns ON the internal switch 32 of the capsule medical apparatus 3A. When the timer 15 starts measuring the time, the capsule medical apparatus 3A is inserted into the body cavity of the patient 2 per oral or per anal. While the capsule medical apparatus 3A advances in the body cavity, the control circuit of the control board 14 reads out first time information measured by the timer 15 and second time information for releasing detection cells 4 set in the memory 34 and compares the two items of time information.

If it is determined that the first time information matches the second time information as a result of this comparison of the time information, the control circuit of the control board 14 reads out from the memory 34 the information about the number of released detection cells 4. Based on the information about the number of released detection cells 4, the control board 14 sends a first control signal for controlling the rotation to the motor 25 and sends a second control signal for adjusting the ratio between the numbers of revolutions of the motor 25 and the cam 24 to the transmission gear 26 via the flexible board 27. When these first and second control signals are sent to the motor 25 and the transmission gear 26, respectively, the cam 24 starts to rotate. At this time, the cam 24 is controlled to exhibit a predetermined rotational speed and a predetermined number of revolutions based on the first and second control signals.

When the cam 24 rotates, as described above, the cutout 22 faces the release slot 28 to cause the detection cell 4 to be guided into the cutout 22 from the storage container 12 by the pressing force of the elastic member 21. When the cam 24 rotates further, the cam surface 30 presses the detection cell 4 accommodated in the cutout 22 to push it towards the release port 18 along the release slot 28. The cam 24 then repeats the above-described release operation by continuing to rotate until a predetermined number of revolutions is reached to release as many detection cells 4 as the number set in the memory 34 into the body cavity, one detection cell 4 at a time.

In this manner, the number of released detection cells 4 is adjusted according to substances to be detected and examination sites in the body cavity. For example, when the main purpose is to examine for intestinal disorders, many detection cells 4 are released in the intestine, whereas few or no detection cells 4 are released in sites other than the intestine, such as the colon. Furthermore, the same number of detection cells 4 may be released in all examination sites.

Each of the detection cells 4 released into the examination sites in the body cavity is immobilized on the inner wall of the body cavity by the leaf springs 45a and 45b, with the shutter 43 closed. The external apparatus 6 then transmits a first signal for instructing the acquisition of reference data towards the body cavity via the external antenna 5. In this case, the plurality of detection cells 4 indwelled at different sites in the body cavity receive the first signal by their respective intracellular antennas 54. Each of the detection cells 4 emits illuminating light onto the reactor tank 57 from the illuminating element 67 for a predetermined period of time and receives, on the photodetector 68, a reference beam that has passed through the reactor tank 57 to store the obtained result as reference data in the memory 55.

Next, the external apparatus 6 transmits a second signal for triggering a reaction between a specimen to be collected and a substance such as an antibody towards the body cavity via the external antenna 5. The plurality of detection cells 4 indwelled at different sites in the body cavity receive the second signal by their respective intracellular antennas 54. The second signal is recognizable to all detection cells 4 released in the body cavity. When each of the detection cells 4 receives the second signal, it opens the shutter 43 by a control signal from the signal processing board 53 to guide a specimen such as a body fluid into the reactor tank 57. When the reactor tank 57 is filled with the specimen, the detection cell 4 closes the shutter 43 and absorbs an antibody into the reactor tank 57 from the reagent container 59 to mix the specimen with the substance such as an antibody for antigen-antibody reaction.

During or after the reaction, the external apparatus 6 transmits a third signal for instructing detection of the reaction result of the antigen-antibody reaction towards the body cavity via the external antenna 5. When the detection cell 4 receives the third signal, it again emits illuminating light onto the reactor tank 57 from the illuminating element 67 and receives, on the photodetector 68, the measuring light that has passed through the reactor tank 57 to store the acquired result as measurement data in the memory 55. The reference data and measurement data stored in the memory 55 are used for an arithmetic operation by the signal processing circuit on the signal processing board 53. The evaluation result output through this arithmetic operation is stored back in the memory 55 as examination data.

In the above-described antigen-antibody reaction, the reaction unit 51 and the reaction-detecting section 52 exhibit a blood sensor function for detecting blood in the specimen using a blood component antibody or a tumor sensor function provided with, for example, an esophageal cancer marker antibody, a gastric cancer marker antibody, or a colon cancer marker antibody.

Blood component antibodies include, for example, antibody conjugated colloid in which anti-human hemoglobin or mouse monoclonal antibody is bound to gold colloid particles and chromogen. The antibody conjugated colloid exhibits red-purple color, and changes its color to light red-purple or gray color when it reacts with human hemoglobin in the specimen and agglutinates. Esophageal cancer markers include SCC, CYFRA, and other substances. Gastric cancer markers include CEA, CA72-4, CA19-9, STN, and other substances.

When a reagent is to be used to detect an antigen, a labeling reagent may be pre-sealed in the reagent container 59, in addition to the antibody. In this case, the labeling reagent is absorbed from the reagent container 59 during or after the reaction to mix the reagent with an antigen-antibody complex generated by the antibody and the antigen in the specimen.

More specifically, the substance such as an antibody is guided into the reactor tank 57 from the reagent container 59 when it starts reacting with the specimen, and reacts with the antigen in the specimen in the reactor tank 57 to cause a change in light transmittance or an optical change such as coloration, discoloration, luminescence, or fluorescence. The presence of, for example, bleeding or tumors is detected by measuring the optical change using the photodetector 68. For example, when a change in light transmittance is to be detected, the detection cell 4 detects a reference beam and measuring light with the photodetector 68 and sends the reference data and the measurement data having information about the respective light intensities to the signal processing board 53. The detection cell 4 compares these items of data in the signal processing circuit of the signal processing board 53, and thereby the post-reaction attenuation of light with respect to the pre-reaction light intensity is calculated.

In a case where luminescence occurs in an antigen-antibody reaction, the luminescence may be detected by the photodetector 68 without emitting illuminating light from the illuminating element 67.

When each of the detection cells 4 in all sites in the body cavity completes the above-described series of reaction detection processes and the evaluation result is stored in the memory 55 as examination data, a command signal, i.e., a fourth signal, for instructing the read-out of the identification code is sent from the external apparatus 6 towards the body cavity. The fourth signal is recognizable to all detection cells 4 released in the body cavity. When each of the plurality of detection cells 4 in the body cavity receives the fourth signal, it transmits externally the identification code stored in the memory 55 via the intracellular antenna 54. Because this identification code contains only a small amount of information, the identifying section of the external apparatus 6 identifies all identification codes in a short time even if all detection cells 4 in the body cavity transmit the identification codes simultaneously. In this manner, a plurality of detection cells 4 are identified by the identifying section in a short time in a non-contact manner.

When the external apparatus 6 identifies all identification codes and determines the number of detection cells 4 existing in the body cavity, the external apparatus 6 sequentially transmits to all detection cells 4 a fifth signal for instructing the transmission of examination data. When each of the detection cells 4 receives the fifth signal, it externally transmits examination data stored in the memory 55 according to a communication protocol. At this time, the plurality of detection cells 4 sequentially transmit examination data based on the communication protocol, one data item at a time. The transmitted examination data and identification codes are received by the external antenna 5, transferred to the external apparatus 6, and are then processed and saved in the PC 85. When in-vivo information at regions in the body is to be displayed, the saved examination data and other information are displayed on the display section 86.

The transmission of the above-described first, second, and third signals is performed by the specimen-evaluation control section (not shown in the figure) provided in the external apparatus 6. Furthermore, the transmission of the above-described fourth signal is performed by the communication control section (not shown in the figure) provided in the external apparatus 6.

Furthermore, in the above-described series of reaction detection processes, the external apparatus 6, if necessary, transmits electromagnetic waves (energy) towards the body cavity via the external antenna 5 to charge the storage batteries 72 in the detection cells 4.

As described above, according to the in-vivo information acquisition apparatus system 1 of this embodiment, a detection cell 4 indwelled in the body cavity receives a reaction start signal and opens the shutter 43 to guide a specimen into the reactor tank 57. Therefore, foreign substances from sites other than an examination site can be prevented from attaching to the reactor tank 57 until reaction is instructed. Consequently, blood (hemoglobin), tumor markers, etc. included in a specimen such as a body fluid can be detected with high accuracy at a plurality of sites in the body cavity to provide highly reliable in-vivo information.

Furthermore, a plurality of detection cells 4 can contain different antibodies, and these detection cells 4 can be sequentially released into the body cavity. Thereby, a plurality of types of substances and antigens included in the specimen can be detected in the same examination site.

The second and fourth signals are recognizable to all detection cells 4 released in the body cavity. Therefore, with a single control operation from the external apparatus 6, a plurality of detection cells 4 can start a reaction of their respective specimens and transmit identification codes substantially at the same time. As a result, a reaction between a specimen and a substance such as an antibody in the body cavity can be started in a plurality of examination sites substantially at the same time.

Furthermore, every detection cell 4 stores a unique identification code in the memory 55, and includes the intracellular antenna 54 for transmitting various types of information, such as the identification code. Therefore, the detection cells 4 distributed at a plurality of sites in the body cavity can be identified all at the same time in a non-contact manner. As a result, even if information about the number of detection cells 4 stored in the capsule medical apparatus 3A is not available, the number of communicable detection cells 4 released into the body cavity can be identified in a short period of time.

Furthermore, because the detection cells 4 transmit examination data to the external antenna 5 according to the communication protocols stored in the memories 55, interference among a plurality of data items can be avoided.

The capsule medical apparatus 3A according to this embodiment stores therein a plurality of detection cells 4 and is transported into the body cavity. Thereby, the detection cells 4 can be released at a plurality of examination sites and indwelled in the body cavity. Furthermore, since the release unit 13 is controlled by the setting information in the memory 34, the number of released detection cells 4 can be adjusted according to the substances to be detected in the body cavity and the purpose of examination. As a result, a desired number of detection cells 4 can be released to a plurality of different examination sites in the body cavity while advancing the capsule medical apparatus 3A.

Furthermore, because a plurality of detection cells 4 can be stored in the capsule medical apparatus 3A, the number of times the capsule medical apparatus 3A is inserted into the body cavity of the patient 2 can be decreased even when two or more sites are to be examined in the body cavity. As a result, the patient 2 feels less discomfort because the capsule medical apparatus 3A needs to be inserted per oral or per anal a smaller number of times. Furthermore, the detection cells 4 are released in a direction substantially perpendicular to the longitudinal direction of the capsule medical apparatus 3A. Therefore, the released detection cells 4 do not block the advance of the capsule medical apparatus 3A, regardless of which end of the casing 11 is in front when the capsule medical apparatus 3A is advanced.

Furthermore, because the capsule medical apparatus 3A includes the electrical connection in the storage container 12, power can be supplied to the detection cells 4 while they are stored in the capsule medical apparatus 3A. As a result, even if the detection cells 4 are stored in the storage container 12 for such a long time as to cause the batteries to be released, the capsule medical apparatus 3A can re-charge the power supplies of the detection cells 4.

Furthermore, because the external apparatus 6 stores data indicating release times of the detection cells 4 set in the timer 15 of the capsule medical apparatus 3A and identification codes of the detection cells 4, the locations of the detection cells 4 in the body cavity can be estimated by associating the release times with the identification codes. As a result, sites where bleeding or a tumor has been confirmed in the body cavity can be more easily identified by associating examination data transmitted by the detection cells 4 with the estimated positions of the detection cells 4. This improves the diagnostic capability.

This embodiment is not limited to the above-described structure.

Figure 8A:
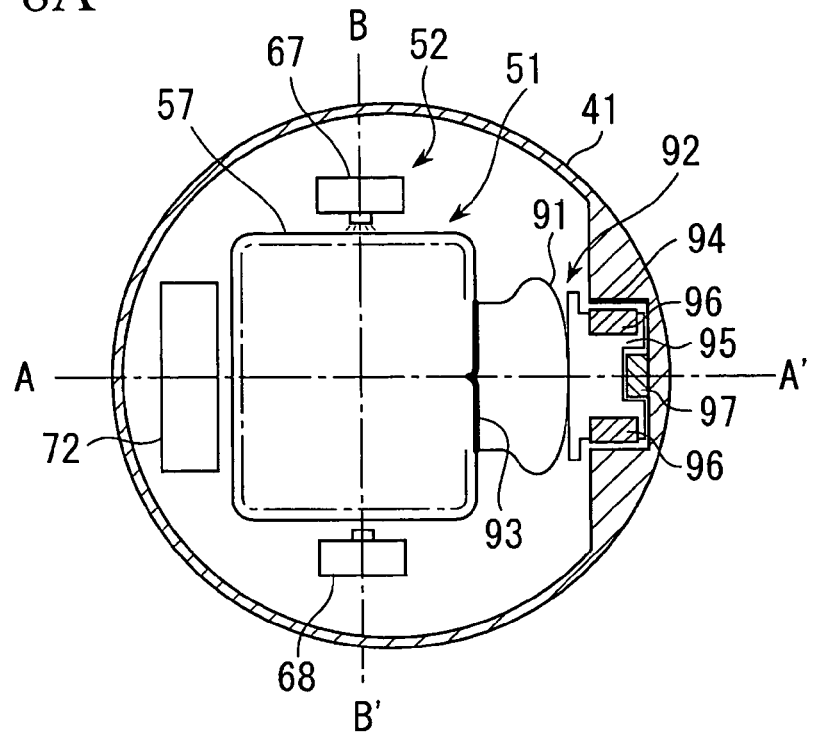
FIG. 8 includes diagrams depicting the internal structure of a detection cell according to a modification of the detection cell shown in FIG. 6.
Figure 8B:
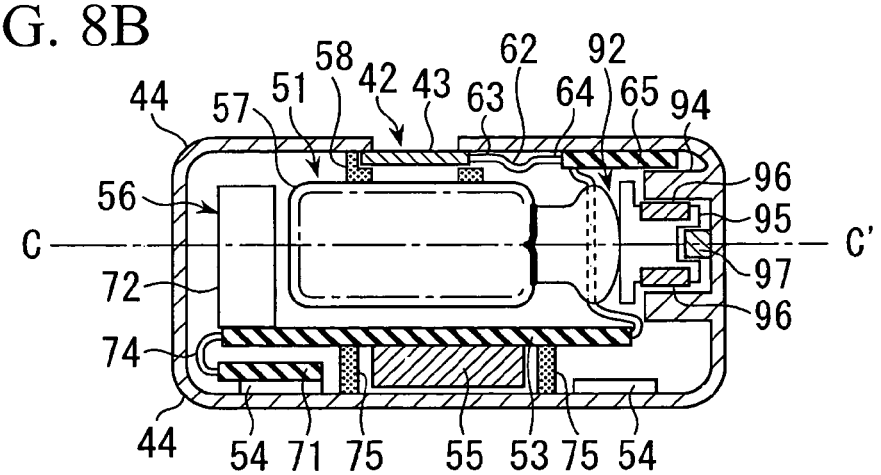
Figure 8C:
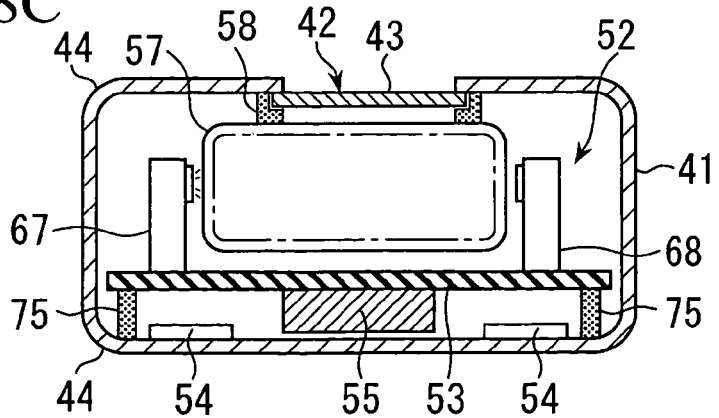

First, according to this embodiment, a substance such as an antibody stored in the reagent container 59 is absorbed into the reactor tank 57 of the reaction unit 51 in each detection cell 4 by the operation of the micropump 61. Instead, an elastic reagent container 91 and a microactuator 92 may be provided, as shown in FIG. 8. In this case, the elastic reagent container 91 is expandable and shrinkable to store a substance such as an antibody in place of the reagent container 59. The microactuator 92 is connected to the drive board 65, and presses the elastic reagent container 91 with a control signal from the signal processing board 53. Furthermore, a gate valve 93 is provided between the reactor tank 57 and the elastic reagent container 91. This gate valve 93 opens only when it is subjected to a pressure equal to or higher than a certain value to allow a fluid such as an antibody to move between the elastic reagent container 91 and the reactor tank 57.

Here, a solenoid actuator provided at a concave mounting portion 94 on the inner surface of the cell enclosure 41 is used as one example of the microactuator 92, as shown in FIG. 8. The solenoid actuator includes at the center thereof a substantially cylindrical pressing member 95, and a coil 96 is wound around the outside of the pressing member 95. Furthermore, a permanent magnet 97 is provided at the mounting portion 94 on the inner surface of the cell enclosure 41. The solenoid actuator applies electrical current to the coil 96 from the signal processing board 53, and thereby the pressing member 95 is moved towards or away from the reactor tank 57 (i.e., in the left or right direction on the figure).

In this structure, when a specimen such as a body fluid is to be reacted with a substance such as an antibody, the detection cell 4 introduces the specimen into the reactor tank 57 and closes the shutter 43. Thereafter, the detection cell 4 drives the microactuator 92 by a control signal. At this time, the microactuator 92 presses the elastic reagent container 91 and moves a substance such as an antibody stored in the elastic reagent container 91 into the reactor tank 57 to mix the specimen with the substance such as an antibody for antigen-antibody reaction.

In this manner, the mechanism for introducing a substance such as an antibody into the reactor tank 57 is simplified to make the structure less complicated, so that the detection cells 4 can be made compact.

Although the microactuator 92 in this figure is shown with a simplified structure, the microactuator 92 can be of any type. More specifically, the microactuator 92 may be realized by a solenoid actuator, as shown in FIG. 8, a standard DC motor or AC motor, a linear motor, or a piezoelectric motor.

Second, according to this embodiment, the leaf springs 45a and 45b are used as an indwelling section. Instead, an indwelling section 102 may be provided near a bottom surface 101, which corresponds to the rear surface of the sampling port 42 of the cell enclosure 41.

Figure 9A:
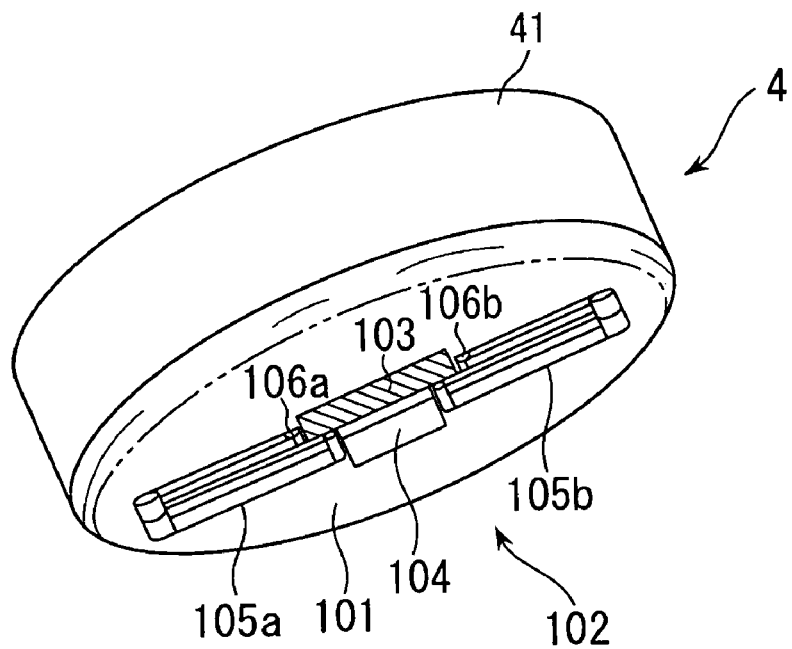
FIG. 9 includes diagrams depicting an indwelling section according to a modification of the detection cell shown in FIG. 5.
Figure 9B:
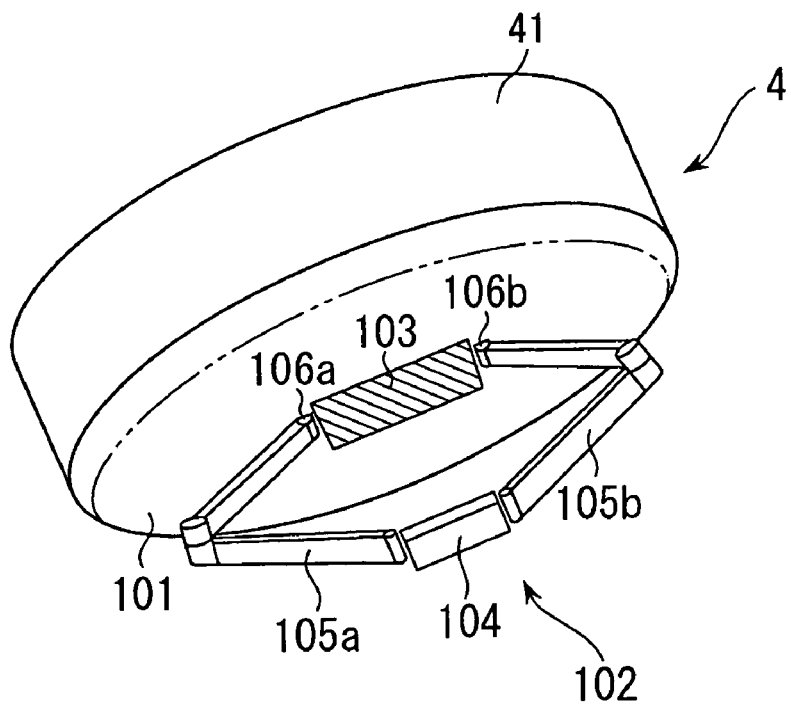

As shown in FIGS. 9A and 9B, the indwelling section 102 includes an electromagnet 103, a magnet 104, and two bendable/stretchable arms 105a and 105b. The electromagnet 103 is provided substantially at the center near the bottom surface 101 of the cell enclosure 41, and includes a coil electrically connected to the above-described signal processing board 53. Furthermore, the magnet 104 is substantially rectangular. It is arranged so as to face the electromagnet 103 and be separated from the electromagnet 103. One end of the arm 105a and one end of the arm 105b are mounted on both ends of this magnet 104. Furthermore, the other ends of the arms 105a and 105b are fixed to arm-mounting portions 106a and 106b, respectively, provided on the bottom surface 101 of the cell enclosure 41.

The electromagnet 103 produces a magnetic attractive or repulsive force with respect to the magnet 104. The magnet 104 can move towards or away from the electromagnet 103 by bending/stretching the two arms 105a and 105b. The signal processing board 53 controls the magnetic field generated by the coil by, for example, reversing the direction in which electrical current flows in the coil of the electromagnet 103. More specifically, the signal processing board 53 controls the magnetic field of the electromagnet 103, and thereby the magnet 104 moves towards or away from the electromagnet 103 as the two arms 105a and 105b bend or stretch. As a result, the detection cell 4 can pinch the inner wall of the body cavity in the space surrounded by the two arms 105a and 105b.

While the detection cell 4 is stored in the storage container 12 of the capsule medical apparatus 3A, the arms 105a and 105b are folded as shown in FIG. 9A. When the detection cell 4 is released into the body cavity from the capsule medical apparatus 3A, the detection cell 4 controls the electromagnet 103 to cause the magnet 104 to experience a repulsive force, as shown in FIG. 9B. At this time, since the arms 105a and 105b stretch, the inner wall of the body cavity is introduced into the space surrounded by the two arms 105a and 105b. Next, the detection cell 4 controls the electromagnet 103 to cause the magnet 104 to experience an attractive force, and thereby the arms 105a and 105b are re-folded. As a result, the inner wall of the body cavity is pinched by the arms 105a and 105b.

With the structure using the above-described indwelling section 102, the signal processing board 53 is controlled to cause the detection cell 4 to actively indwell itself in the body cavity.

Although FIG. 9A shows the arms 105a and 105b folded outside the bottom surface 101 of the cell enclosure 41, the present invention is not limited to this example. Instead, the bottom surface 101 may be provided with a groove for accommodating the arms 105a and 105b. For example, while the arms 105a and 105b are folded, this groove has such a depth that the bottom surface 101 is substantially flush with the outermost surfaces of the arms 105a and 105b. This allows the detection cell 4 to be smoothly released from the capsule medical apparatus 3A into the body cavity. Furthermore, instead of the above-described structure, the indwelling section 102 may have such a structure that the arms 105a and 105b bend/stretch in a direction parallel to the bottom surface 101.

Figure 10:
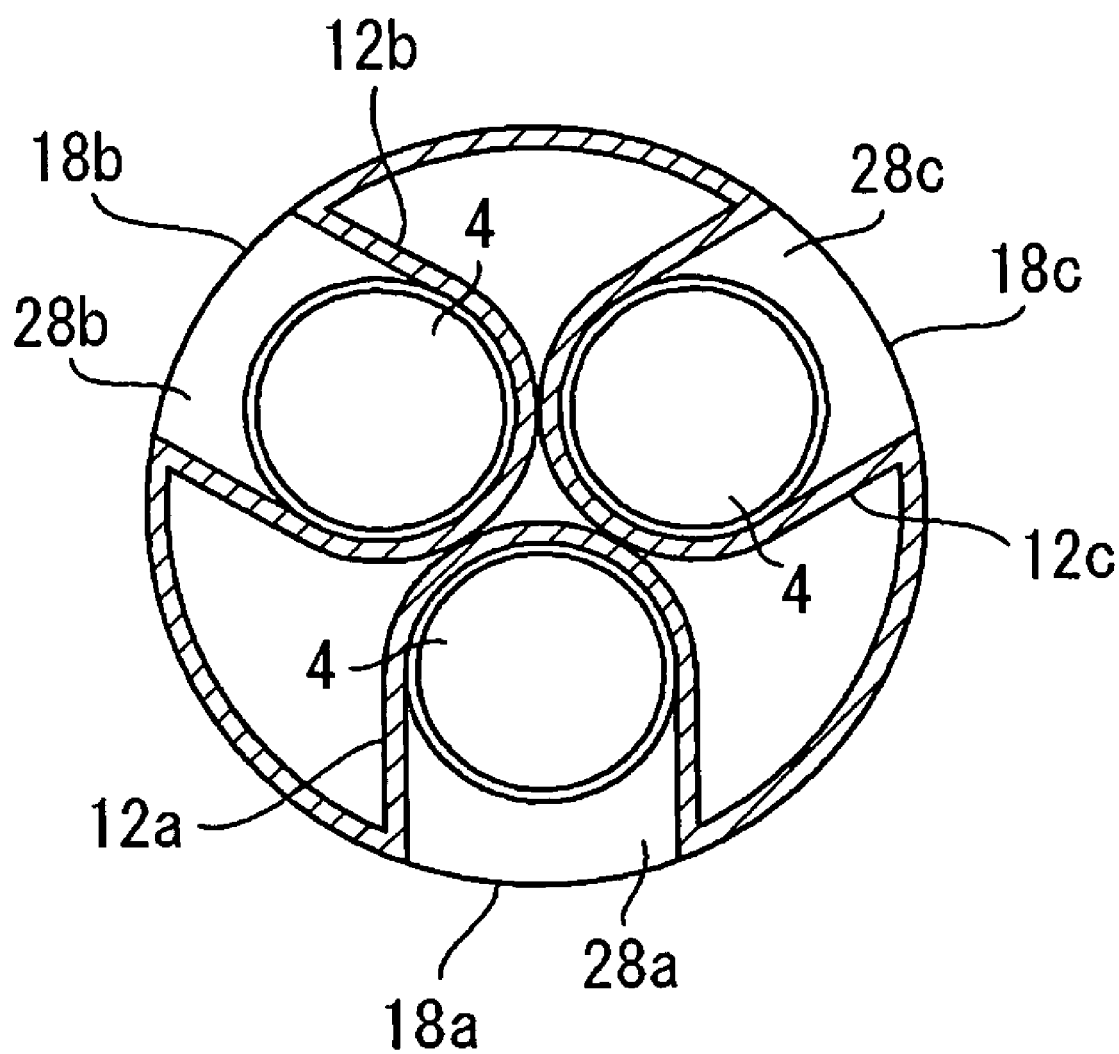
FIG. 10 is a cross-sectional view of the internal structure according to a modification of the capsule medical apparatus shown in FIG. 2.

Third, according to this embodiment, the capsule medical apparatus 3A includes one storage container 12. Instead, the capsule medical apparatus 3A may include a plurality of storage containers 12. For example, as shown in FIG. 10, the capsule medical apparatus 3A includes three storage containers 12a, 12b, and 12c, which are arranged at intervals of approximately 120° about the central longitudinal axis of the casing 11. Furthermore, the storage containers 12a, 12b, and 12c have one open end connected to the cam container 17. This cam container 17 has three release slots 28a, 28b, and 28c formed therein, which are connected to three release ports 18a, 18b, and 18c, respectively provided on the casing 11. The storage containers 12a, 12b, and 12c, the release ports 18a, 18b, and 18c, and the release slots 28a, 28b, and 28c are arranged with the same positional relationships as those of the storage container 12, the release port 18, and the release slot 28.

More specifically, when the cam 24 rotates, the cutout 22 of the cam 24 faces the release slot 28a (28b, 28c) to introduce the detection cell 4 stored in the storage container 12a (12b, 12c) into the cutout 22. When the cam 24 rotates further, the cam surface 30 presses the detection cell 4 accommodated in the cutout 22 to push it towards the release port 18a (18b, 18c) along the release slot 28a (28b, 28c). Thereafter, when the cam 24 rotates by 120°, the cutout 22 faces the release slot 28b (28c, 28a) to cause the detection cell 4 to be released through the same release operation.

Furthermore, the cam 24 then repeats the above-described release operation by continuing to rotate until a predetermined number of revolutions is reached to release the specified number of detection cells 4 into the body cavity, one detection cell 4 at a time.

This enables more detection cells 4 to be stored in the capsule medical apparatus 3A. As a result, the number of times the capsule medical apparatus 3A is inserted into the body cavity of the patient 2 can be decreased even when many sites are to be examined in the body cavity.

Second Embodiment

An in-vivo information acquisition apparatus system according to a second embodiment of the present invention will now be described with reference to FIGS. 11A to 11C, with special attention focused on a detection cell 110. In the second embodiment, the same components as those in the first embodiment are denoted with the same reference numerals, and thus will not be described. Furthermore, for the convenience of description, some components will be described with reference to FIGS. 1, 5, and 9.

The detection cell 110 according to this embodiment differs from the detection cell 4 according to the first embodiment in that the detection cell 110 includes a film 112 having a reaction surface for causing a specimen such as a body fluid to react with a substance such as an antibody (hereinafter, referred to just as the reaction surface), instead of the reactor tank, and an RF-ID 114, instead of the intracellular antenna.

Figure 11A:
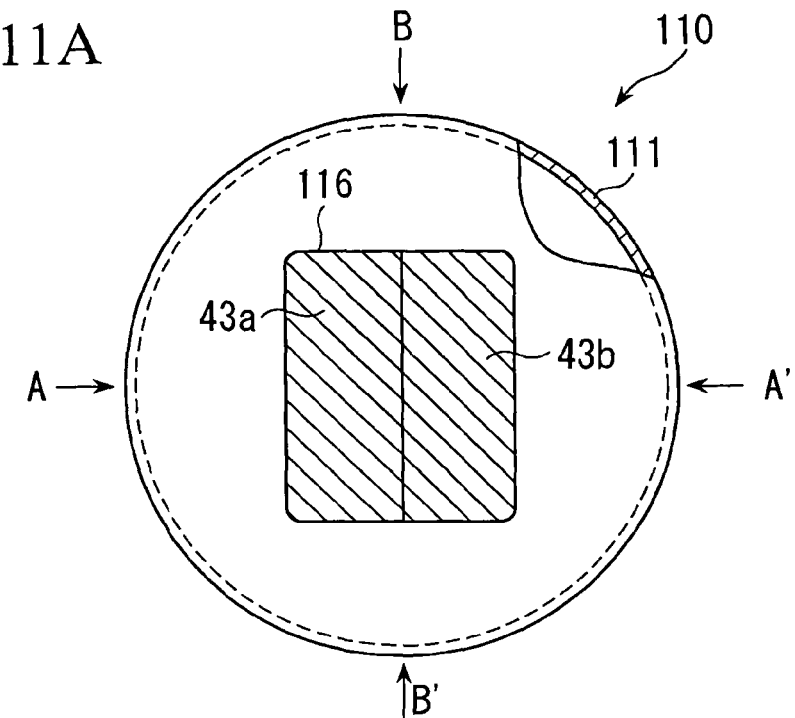
FIG. 11 includes diagrams depicting the internal structure of a detection cell according to a second embodiment of the present invention.
Figure 11B:
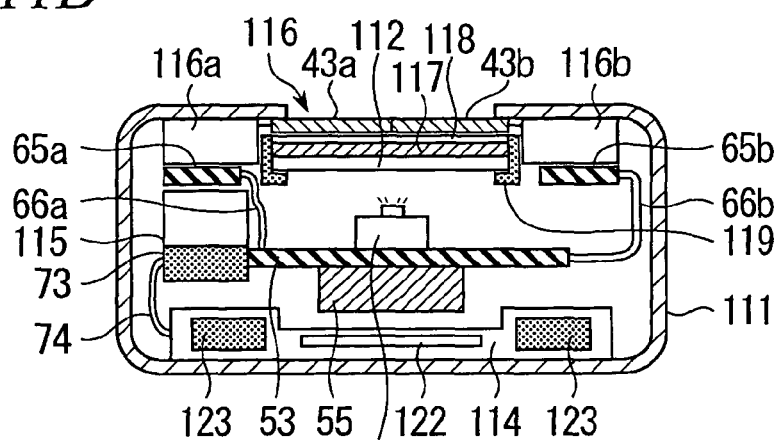
Figure 11C:
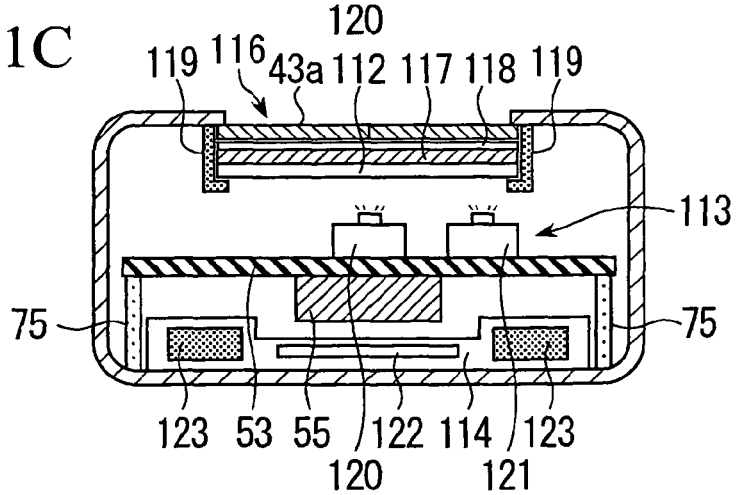

FIG. 11 includes diagrams depicting the structure of the detection cell 110 according to the second embodiment of the present invention. FIG. 11A is a top view of the detection cell 110. FIG. 11B is a cross-sectional view taken along line A-A' of the detection cell 110 in FIG. 11A. FIG. 11C is a cross-sectional view taken along line B-B' of the detection cell 110 in FIG. 11A.

The detection cell 110 includes a disc-shaped cell enclosure 111, and further includes in the cell enclosure 111 the film 112, a reaction-detecting section (specimen-evaluating section) 113, a signal processing board 53, a memory 55, an RF-ID (labeling section, communication section) 114, and a capacitor (power supply section) 115.

The film 112 has a reaction surface used to detect a reaction of a detected substance included in a specimen such as a body fluid collected from the body cavity. Furthermore, the reaction-detecting section 113 is arranged near the film 112 to detect the reaction result of the specimen on the film 112. The signal processing board 53 includes a signal processing circuit for subjecting the internal components of the detection cell 110 to control processing, processing the reaction result from the reaction-detecting section 113, etc. The memory 55 stores in-vivo information acquired in the reaction-detecting section 113, setting information including reaction conditions at the time of examination by the external apparatus 6, etc. The RF-ID 114 is arranged below the signal processing board 53 to exhibit a function for transmitting/receiving a signal for controlling the detection cell 110 and a signal such as in-vivo information to/from the external antenna 5 and for storing identification codes unique to a plurality of detection cells. The capacitor 115 is mounted adjacent to the top surface of the signal processing board 53 to supply operating power to the electrical system in the detection cell 110.

The cell enclosure 111 has an indwelling section including the leaf springs 45a and 45b shown in FIG. 5 or the arms 105a and 105b shown in FIG. 9. Furthermore, as shown in FIG. 11, the cell enclosure 111 has on a surface thereof a substantially rectangular opening (specimen-collecting section) 116 for pulling in a specimen such as a body fluid and two shutters 43a and 43b provided so as to close the opening 116 from inside the cell enclosure 111. The shutters 43a and 43b are opened/closed by linear actuators 116a and 116b connected to drive boards 65a and 65b, respectively. The drive boards 65a and 65b are connected to the signal processing board 53 via the driving flexible boards 66a and 66b, respectively.

The shutters 43a and 43b have on their inner surfaces the substantially rectangular film 112 having a reaction surface used to detect the reaction of a substance to be detected in a specimen. The reaction surface includes several types of layers composed of, for example, a reagent layer 117 containing a dry reagent or a probe, etc. (hereinafter, referred to just as the reagent etc.) that specifically reacts with a substance to be detected, and a filter layer 118 having a porous member for filtering the specimen, in that order from the film 112. Furthermore, both ends of the film 112 are supported by a supporting member 119 so as to fix the film 112 at a certain distance from the signal processing board 53.

The reaction-detecting section 113 in the detection cell 110 includes a pair composed of an illuminating element 120 and a photodetector 121, separated from each other, that are provided on the signal processing board 53 so as to face the film 112. The illuminating element 120 is formed of, for example, a wavelength tunable light source such as a DFB (Distributed Feedback) laser, and illuminates the film 112 with illuminating light. The photodetector 121 is formed of, for example, a PIN photodiode, and detects scattered or reflected light from the film 112. The optical axis of the illuminating element 120 is set so as to be substantially perpendicular to the film 112, and the optical axis of the photodetector 121 is set an angle to the film 112. Furthermore, a light-source driving circuit (not shown) for driving the light-emitting section of the illuminating element 120 to intermittently fire a flash of light is electrically connected to the illuminating element 120.

The RF-ID 114 is used as a labeling tag for identifying the detection cells 110 distributed at a plurality of sites in the body cavity. The RF-ID 114 is a tag-like medium for storing identification codes unique to a plurality of detection cells 110 to enable the plurality of detection cells 110 to be identified at one time by the use of electromagnetic waves in a non-contact manner. As shown in FIGS. 11B and 11C, the RF-ID 114 is embedded near the external surface of the cell enclosure 111. The RF-ID 114 includes therein a chip 122 having a labeling circuit (not shown) and a memory storing a unique identification code and communication protocol. The RF-ID 114 further includes a compact antenna 123 for transmitting/receiving signals such as a control signal of the detection cell 110 and in-vivo information to/from the external antenna 5. Furthermore, the RF-ID 114 is connected to the capacitor 115 and the signal processing board 53 through the flexible board 74 for communication and the selection switch 73. As a result, the chip 122 and the compact antenna 123 in the RF-ID 114 are electrically connected to the capacitor 115 and the signal processing board 53.

The RF-ID 114 is provided with a communication circuit for selectively extracting electromagnetic waves coming from the external antenna 5, received with the compact antenna 123, for wave detection, demodulating a control signal from the external apparatus 6, and outputting the demodulated signal to, for example, the circuit of each component. Furthermore, the communication circuit has a function for modulating signals from the circuits of the components, such as examination data and an identification code, based on a carrier wave with a predetermined frequency and transmitting electromagnetic waves to the external antenna 5 as in-vivo information from the compact antenna 123. The communication circuit controls the transmission of examination data from a plurality of detection cells 110 through the use of the communication protocol pre-stored in the memory of the chip 122

When examination data is to be read from a plurality of detection cells 110, a command signal for reading in-vivo information by using electromagnetic waves is emitted from the external antenna 5 over a wide region of the body. A plurality of detection cells 110 existing in the radiation area of the electromagnetic waves receive the command signal with their respective compact antennas 123. The command signal received with each of the compact antennas 123 is sent as an electrical signal to the chip 122 via the communication circuit of the RF-ID 114. At this time, the RF-ID 114 reads out the identification code and examination data stored in the memory of the chip 122 and sends them to the compact antenna 123 according to the communication protocol. The identification code and the examination data are transmitted externally as electromagnetic waves from the compact antenna 123. Outside the body, through the use of the external antenna 5 and the external apparatus 6, the plurality of detection cells 110 are identified in a short in a non-contact manner by reading and analyzing the identification codes transmitted from the plurality of compact antennas 123.

The capacitor 115 is used as a power supply for feeding the electrical system in the detection cell 110 with operating power. As shown in FIG. 11, the capacitor 115 is connected to the signal processing board 53 via the selection switch 73, and therefore, the operating power of the capacitor 115 is fed to the circuit of each component via the signal processing board 53. Furthermore, a flexible board 74 for communication is connected between the selection switch 73 and the RF-ID 114 so that signals can be transmitted between the capacitor 115, the signal processing board 53, and the RF-ID 114. The capacitor 115 can be charged by, for example, receiving with the RF-ID 114 electromagnetic waves emitted from the external antenna 5 towards the body cavity and transmitting an electrical signal acquired as a result of the reception to the capacitor 115 via the flexible board 74 for communication. Switching between supplying power to the circuit of each component and charging through the RF-ID 114 is achieved with the selection switch 73.

As the capacitor 115, for example, an electrical double-layer capacitor is used. This electrical double-layer capacitor is a compact, high-electrical-capacitance capacitor, and therefore, the capacitor 115 can be made compact without reducing the power supply capacity.

The operation according to this embodiment will now be described.

The detection cell 110 released into the examination site in the body cavity by the capsule medical apparatus 3A is fixed on the inner wall in the body cavity by the indwelling section such as the leaf springs 45$a$ and 45$b$ or the arms 105$a$ and 105$b$, with the shutters 43$a$ and 43$b$ closed. The external apparatus 6 then transmits a first signal for instructing the acquisition of reference data towards the body cavity via the external antenna 5. In this case, the plurality of detection cells 110 indwelled at different sites in the body cavity receive the first signal by their respective RF-IDs 114. Each of the detection cells 110 emits illuminating light onto the film 112 from the illuminating element 120 for a predetermined period of time and receives, on the photodetector 121, a reference beam reflected or scattered at the film 112 to store the obtained result as reference data in the memory 55.

Next, the external apparatus 6 transmits a second signal for triggering a reaction between a specimen to be collected and a substance such as an antibody towards the body cavity via the RF-ID 114. In this case, the plurality of detection cells 110 indwelled at different sites in the body cavity receive the second signal by their respective RF-IDs 114. The second signal is recognizable to all detection cells 110 released in the body cavity. When each of the detection cells 110 receives the second signal, it opens the shutters 43$a$ and 43$b$ by a control signal from the signal processing board 53 to guide a specimen such as a body fluid onto the film 112. The detection cell 110 brings the specimen into contact with, for example, the reagent stored in the reagent layer 117 of the film 112 for reaction detection.

During or after the reaction, the external apparatus 6 transmits a third signal for instructing the detection of a reaction result in the antigen-antibody reaction towards the body cavity via the RF-ID 114. When the detection cell 110 receives the third signal, it again emits illuminating light onto the film 112 from the illuminating element 120 and receives, on the photodetector 121, the measuring light reflected or scattered at the film 112 to store the acquired result as measurement data in the memory 55. The reference data and measurement data stored in the memory 55 are used for an arithmetic operation by the signal processing circuit on the signal processing board 53. The evaluation result output through this arithmetic operation is stored back in the memory in the chip 122 incorporated in the RF-ID 114 as examination data.

In the above-described reaction detection, the film 112 functions as a protein sensor for detecting a particular protein, an enzyme sensor for detecting a particular enzyme, or a DNA sensor for identifying particular DNA.

In a case where a protein is to be detected, a dry reagent that causes an optical change when it reacts with a particular protein is stored in the reagent layer 117, and the reagent in the reagent layer 117 is brought into contact with protein in the specimen to allow the photodetector 121 to detect the optical change. In particular, when an enzyme is to be detected, a receptor that specifically binds with a particular enzyme can be used, so that the receptor binds with the enzyme in the specimen. When the film 112 is illuminated with illuminating light from the illuminating element 120, the weight of the enzyme increases and the Brownian motion becomes slower. Hence, the degree of modulation of the frequency, the phase, etc. of scattered light due to the enzyme motion changes. This modulation of scattered light is measured before and after the binding of the receptor to the photodetector 121, and a change in the modulation of scattered light is calculated to detect the enzyme.

When DNA is to be identified, a solid DNA probe labeled with fluorescent dye is stored in the reagent layer 117. If DNA to be detected exists in the specimen, contact of the specimen with the reagent layer 117 causes the DNA probe to bind with the DNA to be detected, emitting fluorescence. Thus, DNA is detected by measuring the fluorescence at the photodetector 121. It is possible to store only one type of DNA probe in the reagent layer 117. Alternatively, the reagent layer 117 may be formed in an array, so that different DNA probes are stored in each segment. This allows many types of DNA to be detected with a single measurement.

Furthermore, in the same manner as with the above-described DNA sensor, the film 112 may have a function for identifying nucleic acid or RNA.

When each of the detection cells 110 in all sites in the body cavity completes the above-described series of reaction detection processes and the evaluation result is stored as examination data in the memory in the chip 122 incorporated in the RF-ID 114, a command signal, i.e., a fourth signal, for instructing the read-out of the identification code is sent from the external apparatus 6 towards the body cavity. The fourth signal is recognizable to all detection cells 110 released in the body cavity. When each of the plurality of detection cells 110 in the body cavity receives the fourth signal, it transmits externally the identification code stored in the memory in the chip 122 via the RF-ID 114. Because this identification code has only a small amount of information, the external apparatus 6 can identify all identification codes in a short time even if all detection cells 110 in the body cavity transmit the identification codes simultaneously.

When the external apparatus 6 identifies all identification codes and determines the number of detection cells 110 existing in the body cavity, the external apparatus 6 sequentially transmits to all detection cells 110 a fifth signal for instructing the transmission of examination data. When each of the detection cells 110 receives the fifth signal, it externally transmits examination data stored in the memory in the chip 122 according to the communication protocol. At this time, the plurality of detection cells 110 sequentially transmit examination data based on the communication protocol, one data item at a time. The transmitted examination data and identification codes are received by the external antenna 5, are transferred to the external apparatus 6, and are then processed and saved in the PC 85.

Furthermore, in the above-described series of reaction detection processes, the external apparatus 6, if necessary, transmits electromagnetic waves (energy) towards the body cavity via the external antenna 5 to charge the capacitor 115 in the detection cell 110.

According to the in-vivo information acquisition apparatus system of this embodiment with the above-described structure, an antigen-antibody reaction can be produced without a complicated mechanism by using the film 112 that has a reaction surface storing a dry antibody to be reacted with the antigen included in the specimen. Consequently, the detection cells 110 can be made compact, and therefore, the capsule medical apparatus 3A can store more detection cells. Furthermore, since the film 112 is arranged close to the opening 116, a specimen, even if highly viscous, can be reliably introduced onto the film 112 for reaction detection.

Furthermore, each of the detection cells 110 stores a unique identification code in the chip 122 of the RF-ID 114, and includes the compact antenna 123 for transmitting various types of information such as the identification code. Therefore, the detection cells 110 distributed at a plurality of sites in the body cavity can be identified all at once in a non-contact manner. As a result, even if information about the number of detection cells 110 stored in the capsule medical apparatus 3A is not available, the number of communicable detection cells 110 released into the body cavity can be identified in a short period of time. Furthermore, since examination data and a communication protocol are stored in the chip 122, the transmission of examination data from the detection cell 110 can be controlled by the RF-ID 114. This facilitates communication control processing. In addition, the RF-ID 114 is a known identification tag, and therefore an inexpensive and compact detection cell can be provided.

Figure 12A:
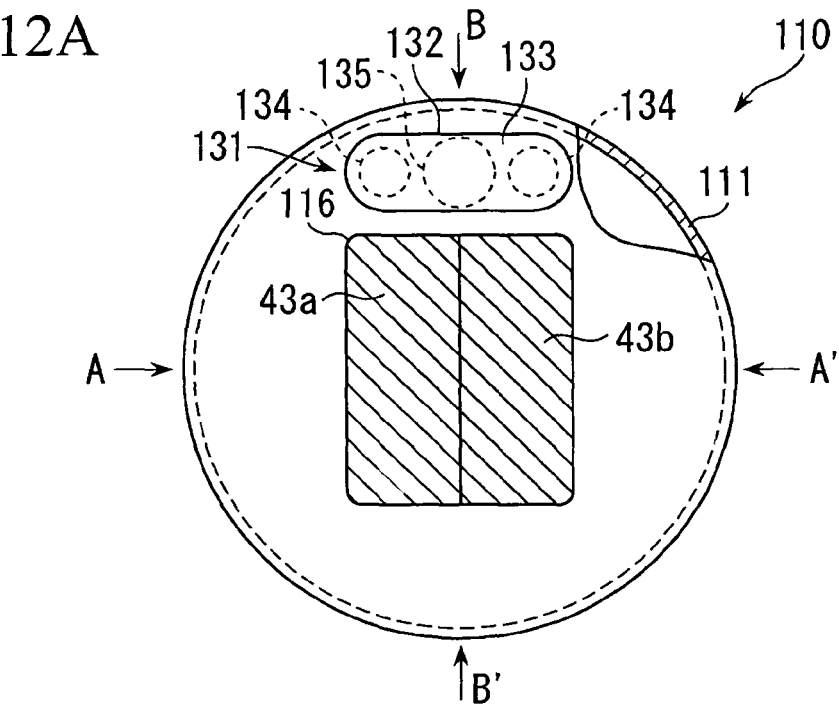
FIG. 12 includes diagrams depicting the internal structure of a detection cell according to a modification of the detection cell shown in FIG. 10.
Figure 12B:
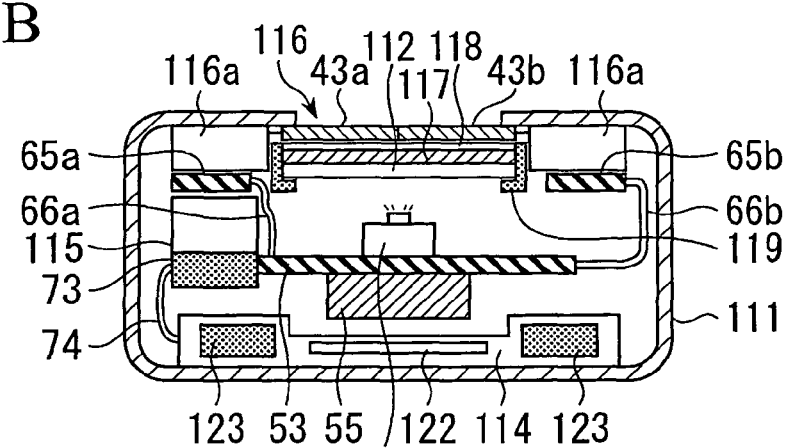
Figure 12C:
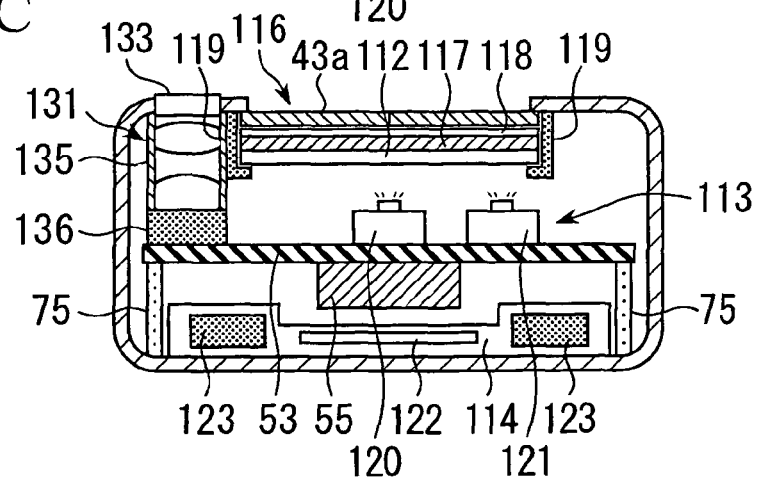

According to this embodiment, as shown in FIG. 12, the detection cell 110 may contain an imaging device 131 for acquiring an image in the body cavity. More specifically, a transparent cover 133 is connected and water-tightly fixed to an opening 132 for imaging provided on part of the surface of the cell enclosure 111, and a pair of illuminating optical systems 134 having an illuminating element for illuminating the body cavity and an imaging optical system 135 including an objective lens are provided at a position opposed to the transparent cover 133 in the hermetic detection cell 110. Furthermore, the signal processing board 53 is provided with an imaging unit 136, and an imaging element included in the imaging unit 136 is arranged on the image formation surface of the imaging optical system 135. The imaging element is realized by, for example, a CMOS (Complementary Metal-Oxide Semiconductor) imager, and the CMOS imager is electrically connected to the signal processing board 53. More specifically, the signal processing board 53 performs driving control of the illuminating element and subjects an image signal output from the CMOS imager to signal processing and control processing.

As a result, image information about the body cavity can be acquired in addition to the detection of examination substances from a specimen. This can provide more detailed in-vivo information which leads to higher-accuracy diagnosis.

Furthermore, according to this embodiment, a wavelength tunable light source, such as a DFB laser, is used as the illuminating element 120. Instead, for example, a narrow-band light source unit for sequentially emitting three colors R (red), G (green), and B (blue) may be used.

Figure 13:
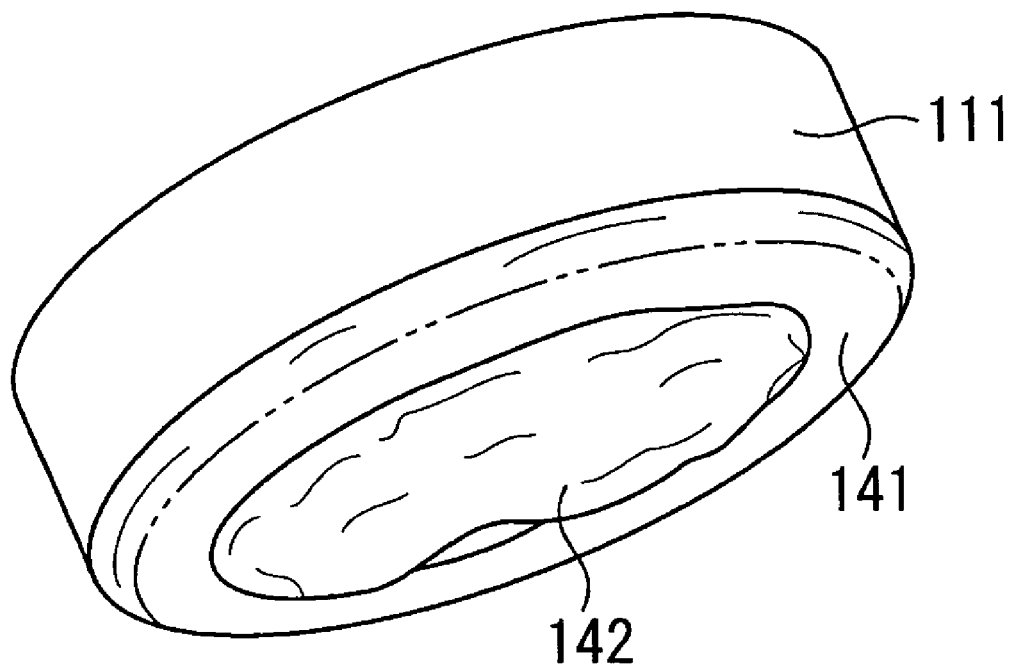
FIG. 13 is a diagram depicting an indwelling section according to a modification of the detection cell shown in FIG. 10.

In addition, as a device for indwelling the detection cell 110 in the body cavity, a biocompatible adhesive (hereinafter, referred to just as an adhesive) may be used instead of the leaf springs 45a and 45b or the arms 105a and 105b. In this case, as shown in FIG. 13, an adhesive container (adhesive release section) 142 made of a soluble flexible member may be attached to the exterior of the bottom surface 141 corresponding to the rear surface of the opening 116 of the cell enclosure 111 to store an adhesive in the adhesive container 142.

When the detection cell 110 is released from the capsule medical apparatus 3A into the body cavity, the adhesive container 142 is dissolved by a body fluid in the body cavity to cause the adhesive stored in the adhesive container 142 to flow out. At this time, the adhesive is disposed between the bottom surface 141 of the cell enclosure 111 and the tissue surface in the body cavity, and thereby the detection cell 110 can be indwelled in the body cavity.

With the above-described structure, the adhesive container 142 is provided outside the cell enclosure 111. Instead, a container for storing an adhesive may be provided in the interior near the bottom surface 141 of the cell enclosure 111. In this case, the adhesive stored in the container is released out of the detection cell 110 with, for example, an actuator. At this time, because the adhesive is disposed between the bottom surface 141 of the cell enclosure 111 and the tissue surface in the body cavity, the detection cell 110 can be indwelled in the body cavity.

Third Embodiment

A capsule medical apparatus according to a third embodiment of the present invention will now be described with reference to FIGS. 14 and 15. In the third embodiment, the same components as those in the first embodiment are denoted with the same reference numerals, and thus will not be described.

Figure 14:
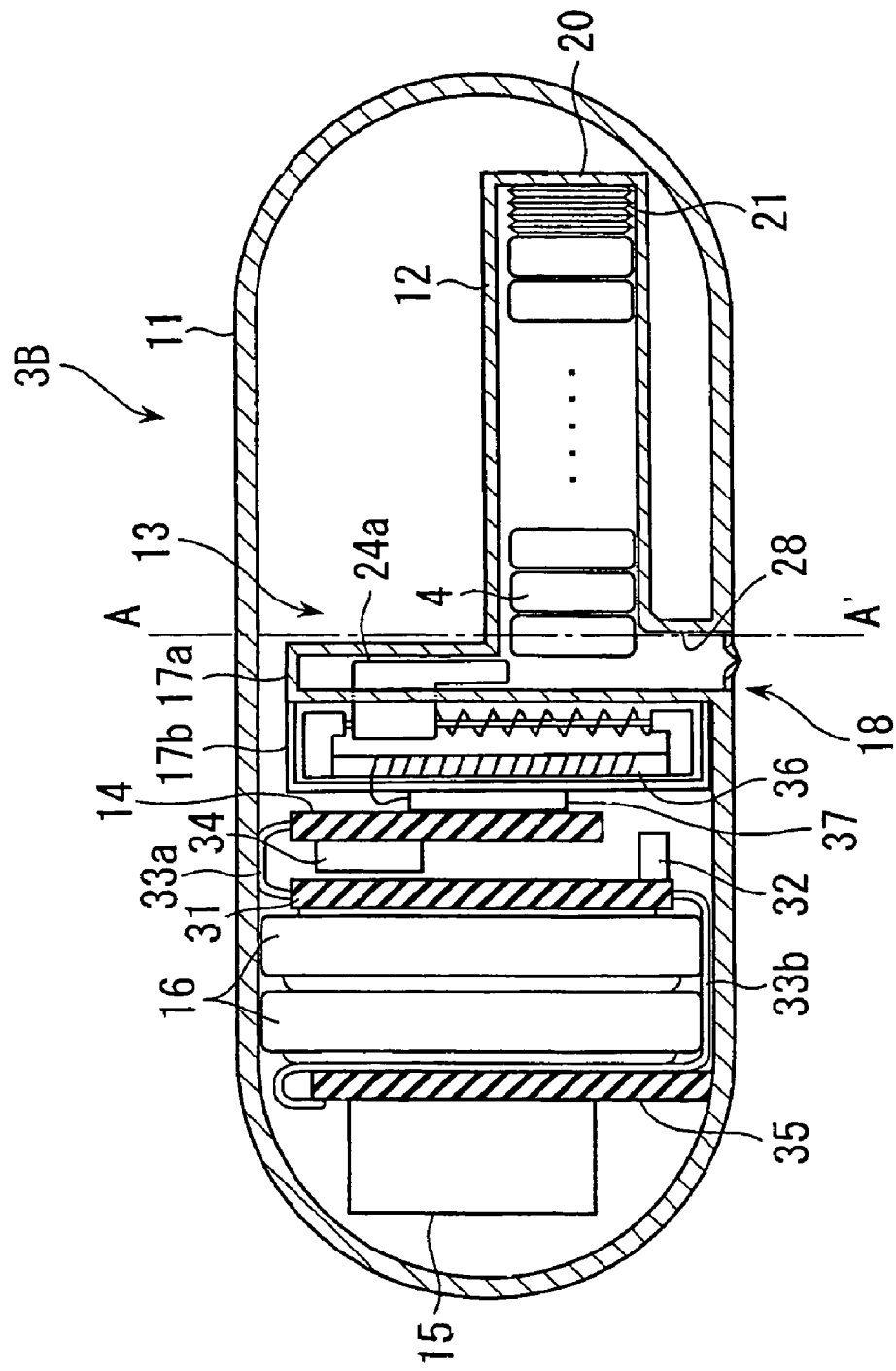
FIG. 14 is a diagram depicting the internal structure of a capsule medical apparatus according to a third embodiment of the present invention.

FIG. 14 is a diagram depicting the internal structure of a capsule medical apparatus 3B according to the third embodiment of the present invention. FIG. 15 is a diagram depicting a magnified detailed view of the structure of the release unit 13.

In this embodiment, the capsule medical apparatus 3B differs from the capsule medical apparatus 3A according to the first embodiment in that the release unit 13 provided near the center of the casing 11 of the capsule medical apparatus 3B includes a mobile object 24a, an electromagnetic solenoid 36, a magnetic-shielding frame 17b, and an oscillator 37, as shown in FIG. 14.

The electromagnetic solenoid 36 is magnetizable in the direction perpendicular to the neutral axis of this casing 11, and has a function for electromagnetically moving the mobile object 24a. Furthermore, the magnetic-shielding frame 17b is arranged adjacent to a mobile object container 17a connected to one open end of the storage container 12 and encloses the electromagnetic solenoid 36 to prevent it from being affected by an external magnetic field. Furthermore, an oscillator 37 is electrically connected to the electromagnetic solenoid 36 and the control board (control section) 14.

Figure 15:
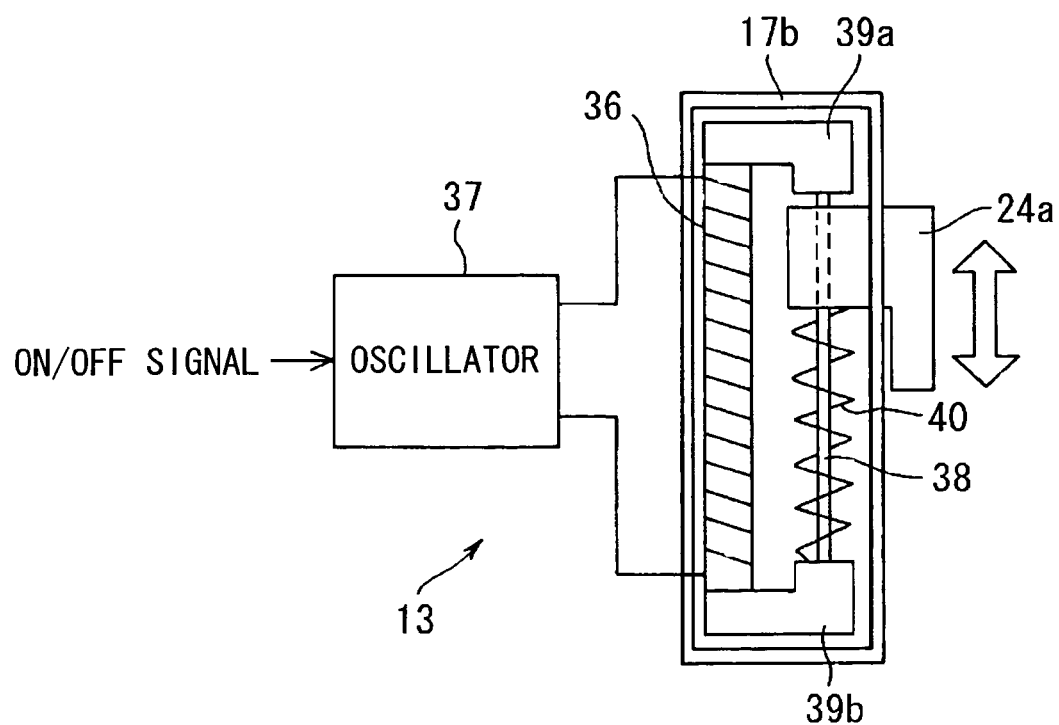
FIG. 15 is a diagram depicting a release unit of the capsule medical apparatus shown in FIG. 14.

As shown in FIG. 15, the electromagnetic solenoid 36 and the guiding member 38 arranged parallel to this electromagnetic solenoid 36 are connected and fixed with retaining members 39a and 39b. The mobile object 24a having a hole through which the guiding member 38 passes is mounted on the guiding member 38 such that it is movable in the axial direction of the guiding member 38, and a coil-shaped spring 40 arranged below the mobile object 24a urges the mobile object 24a upward. The retaining member 39a is formed of a non-magnetic object and the retaining member 39b is formed of a magnetic object.

The mobile object 24a is realized by, for example, a magnet, and is supported by the guiding member 38 so as to be movable in the magnetization direction of the electromagnetic solenoid 36. Furthermore, part of the mobile object 24a protrudes from a hole provided on part of the magnetic-shielding frame 17b, and pushes the detection cell 4 guided by the mobile object container 17a. The electromagnetic solenoid 36 can reciprocate the mobile object 24a in the axial direction of the guiding member 38 against the elastic force of the spring 40 that urges the mobile object 24a towards one end (upward in FIGS. 14 and 15) of the guiding member 38. With the downward movement of the reciprocation of this mobile object 24a, the part of the mobile object 24a protruding from the magnetic-shielding frame 17b pushes the detection cell 4 to move it towards the release port 18.

The control board 14 transmits an ON/OFF signal to an oscillator 37 to oscillate the oscillator 37 at a predetermined frequency. This oscillator 37 generates electrical current for driving the electromagnetic solenoid 36 in a frequency range of DC to several Hz.

The driving conditions of the oscillation frequency of the oscillator 37 may be preset, or may be controlled from the control board with a structure that allows a frequency signal to be input in addition to the ON/OFF signal.

The operation according to this embodiment will now be described.

When the capsule medical apparatus 3B is inserted into the body cavity of the patient 2 per oral or per anal, the control circuit of the control board 14 compares first time information measured by the timer 15 with second time information for releasing detection cells 4 set in the memory 34. If it is determined that the first time information matches the second time information as a result of this comparison of the time information, the control circuit of the control board 14 reads out from the memory 34 the information about the number of released detection cells 4.

Based on the information about the number of released detection cells 4, the control board 14 sends the ON/OFF signal to the oscillator 37, and generates electrical current for driving the electromagnetic solenoid 36 in a frequency range of DC to several Hz. When the output signal of the oscillator 37 is applied to the electromagnetic solenoid 36 as a driving signal, the electromagnetic solenoid 36 generates a magnetic field. Then, with the magnetic field generated by the electromagnetic solenoid 36, the mobile object 24a is reciprocated in the axial direction of the guiding member 38 against the elastic force of the spring 40.

During downward movement of the reciprocation of this mobile object 24a, part of the mobile object 24a protruding from the magnetic-shielding frame 17b presses the detection cell 4 to push it towards the release port 18. The mobile object 24a then repeats the above-described release operation by continuing to reciprocate a predetermined number of times to release the specified number of detection cells 4 from the storage container 12 into the body cavity, one detection cell 4 at a time.

According to the above-described release operation of the detection cells 4, the electromagnetic solenoid 36 reciprocates the mobile object 24a a predetermined number of times with a control signal sent to the oscillator 37 from the control board 14. This enables the capsule medical apparatus 3B to release a desired number of detection cells to examination sites in the body cavity.

Fourth Embodiment

A capsule medical apparatus and a capsule medical apparatus system according to a fourth embodiment of the present invention will now be described with reference to FIGS. 16 and 17. In the fourth embodiment, the same components as those in the first embodiment are denoted with the same reference numerals, and thus will not be described.

Figure 16:
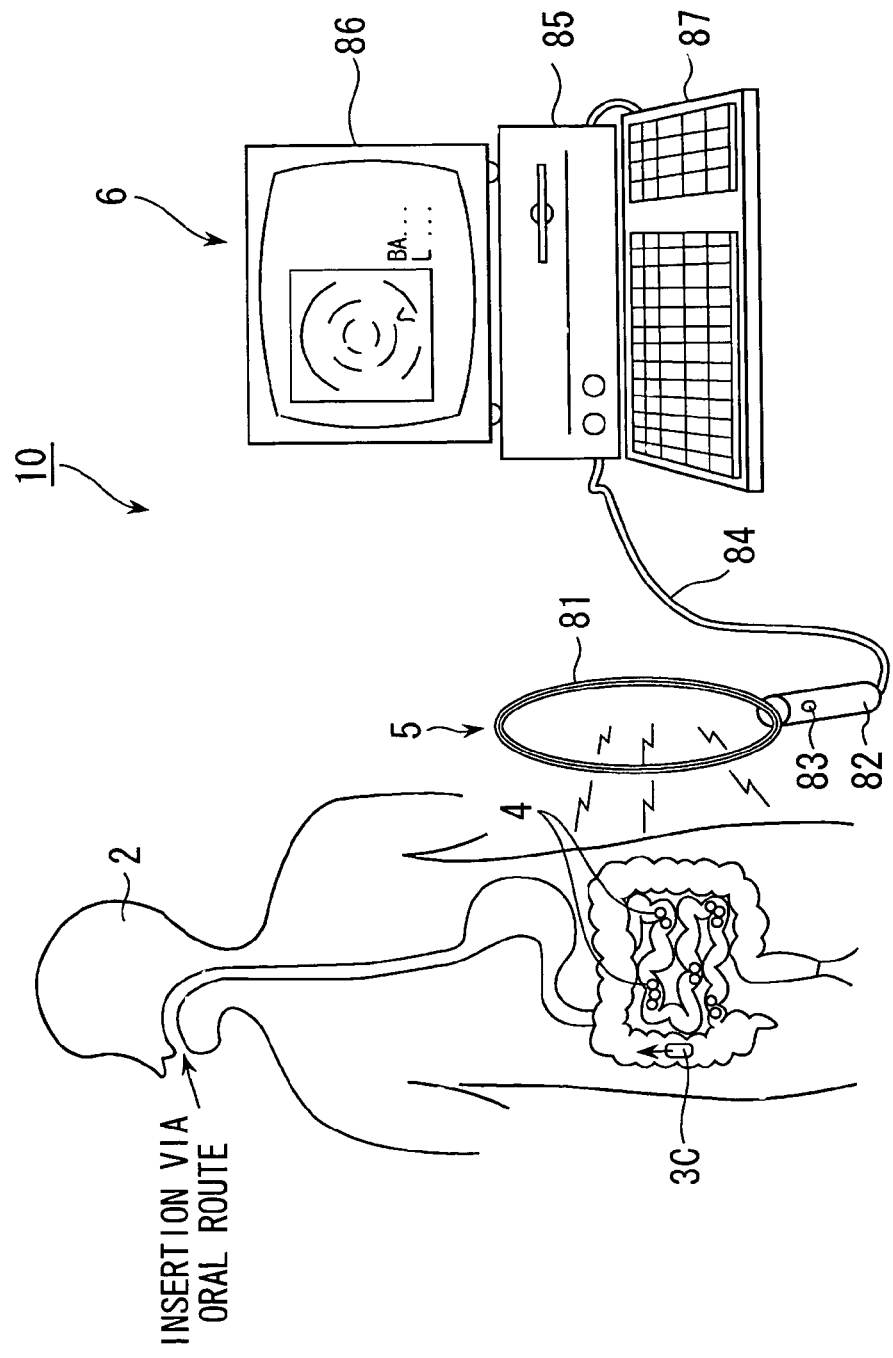
FIG. 16 is a schematic diagram depicting the overall structure of a capsule medical apparatus system according to a fourth embodiment of the present invention.

FIG. 16 is a schematic diagram depicting a capsule medical apparatus system 10 according to the fourth embodiment of the present invention. FIG. 17 is a diagram depicting the internal structure of a capsule medical apparatus 3C used in the capsule medical apparatus system 10 according to this embodiment.

Referring to FIG. 16, the capsule medical apparatus system 10 includes a capsule medical apparatus 3C, detection cells (in-vivo information acquisition apparatuses) 4, an external antenna 5, and an external apparatus 6.

In this embodiment, the capsule medical apparatus 3C differs from the capsule medical apparatus 3A according to the first embodiment in that the capsule medical apparatus 3C has an imaging function. More specifically, as shown in FIG. 17, the capsule medical apparatus 3C has a casing 11 formed like a capsule, and includes a storage container 12, a release unit 13, a control board (control section) 14, batteries 16, an imaging section 191, and a wireless communication antenna 192 in the casing 11.

The imaging section 191 has functions for imaging the interior of the body cavity and for sending the acquired image data to the control board 14. The wireless communication antenna 192 transmits/receives a control signal of the capsule medical apparatus 3C and a signal such as location information in the body cavity to/from the external antenna 5.

Figure 17:
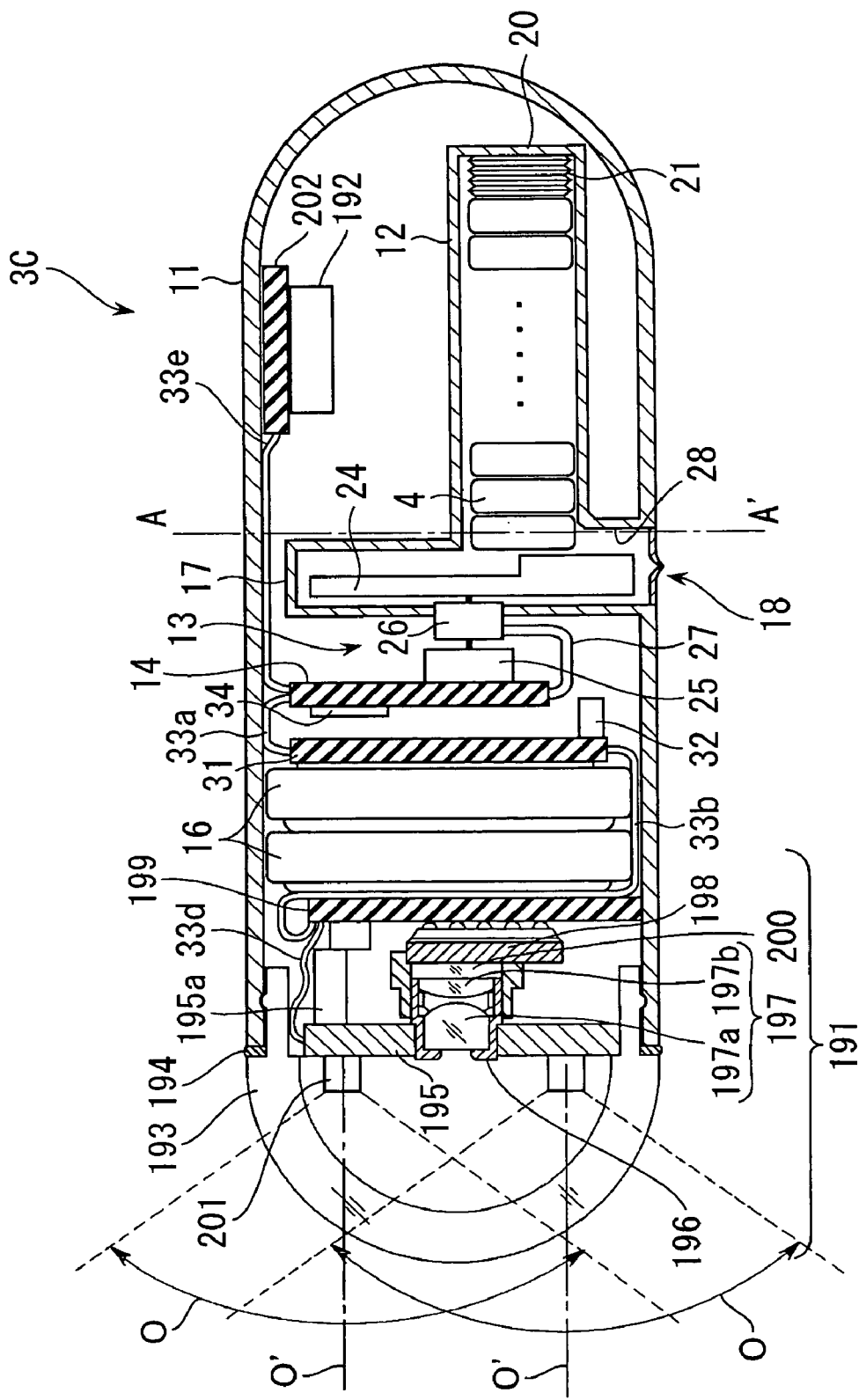
FIG. 17 is a diagram depicting the internal structure of a capsule medical apparatus in the capsule medical apparatus system shown in FIG. 16.

As shown in FIG. 17, in the capsule medical apparatus 3C, a hemispherical transparent cover 193 is connected and water-tightly fixed to one end of the casing 11, and is hermetically sealed with a sealing member 194 in the casing 11. The hermetically sealed capsule container contains therein components of the imaging section 191. The transparent cover 193 is made of synthetic resin such as polycarbonate, cyclo olefin polymer, or PMMA (polymethylmethacrylate)

An objective lens frame. 196 is fitted to a through-hole formed in the center on an illuminating board 195 opposed to the transparent cover 193. An objective optical system 197 formed of a first lens 197a and a second lens 197b is arranged on this objective lens frame 196. Furthermore, for example, a CMOS (Complementary Metal-Oxide Semiconductor) imager 198 is arranged as an imaging device in the image-forming position of the objective optical system 197. This CMOS imager 198 is mounted on the front face of the imaging board 199 arranged behind the illuminating board 195. The imaging surface of the CMOS imager 198 is protected by a cover glass 200.

The imaging board 199 is integrated with the CMOS imager 198 and the cover glass 200. The imaging board 199 includes a signal processing circuit for driving the CMOS imager 198 in response to a signal from the control board 14 and subjecting an image signal output from the CMOS imager 198 to signal processing and control processing.

Furthermore, illuminating sections 201 provided with, for example, white light LEDs that generate white light are mounted on the front face of the illuminating board 195 symmetrically with respect to the objective optical system 197. Symbols O' in the figure represent the central axis (direction defined by an emission angle of 0°) of the luminescence of illuminating light from the light-emitting sections of the illuminating sections 201, and symbols O represent a luminescence range of illuminating light from the light-emitting sections of the illuminating sections 201.

Furthermore, the illuminating board 195 has on its rear surface a chip component 195a constituting an LED driving circuit (not shown) for driving the light-emitting section of the illuminating sections 201 to intermittently fire a flash of light.

The illuminating board 195 is electrically connected to the imaging board 199 via a flexible board 33d. Furthermore, the imaging board 199 is electrically connected to the control board 14 via a flexible board 33b and a power supply board 31. In this manner, the components of the imaging section 191 mounted on the illuminating board 195 and the imaging board 199 can be controlled by a control signal from the control board 14. Furthermore, an image signal output from the CMOS imager 198 is sent to the control board 14, and saved as image data in the memory 34 connected to the control board 14.

The above-described wireless communication antenna 192 is fixed to a wireless board 202 arranged near the internal storage container 12 of the casing 11. Furthermore, the wireless board 202 is electrically connected to the control board 14 via a flexible board 33e.

The wireless board 202 is provided with a wireless circuit for selectively extracting electromagnetic waves coming from the external antenna 5, received with the wireless communication antenna 192, for wave detection, demodulating a control signal from the external apparatus 6, and outputting the demodulated signal to, for example, the circuit of each component. Furthermore, the wireless circuit has a function for modulating information (data) signals such as image data from the circuit of each component based on a carrier wave with a predetermined frequency, and transmitting them as electromagnetic waves to the external antenna 5 from the wireless communication antenna 192.

As shown in FIG. 16, the external apparatus 6 includes, for example, a personal computer (hereinafter, abbreviated as the PC) 85. The PC 85 includes an internal hard disk (not shown) that saves image data acquired from the external antenna 5 and a determination circuit (determination unit) for detecting the location of the capsule medical apparatus 3C. Connected to the PC 85 are a display section 86 for displaying images saved in the hard disk during or after examination and a keyboard 87 as an example of an operating panel for entering data.

Furthermore, when the location of the capsule medical apparatus 3C is to be detected, the external antenna 5 arranged at an extracorporeal location near the examination site receives a signal of image data transmitted from the capsule medical apparatus 3C in the body cavity and transmits it to the external apparatus 6. The image data is used by the determination circuit incorporated in the PC 85 of the external apparatus 6 to detect the location of the capsule medical apparatus 3C.

The imaging section 191 of the capsule medical apparatus 3C and the determination circuit of the PC 85 constitute a position-detecting section.

Figure 18:
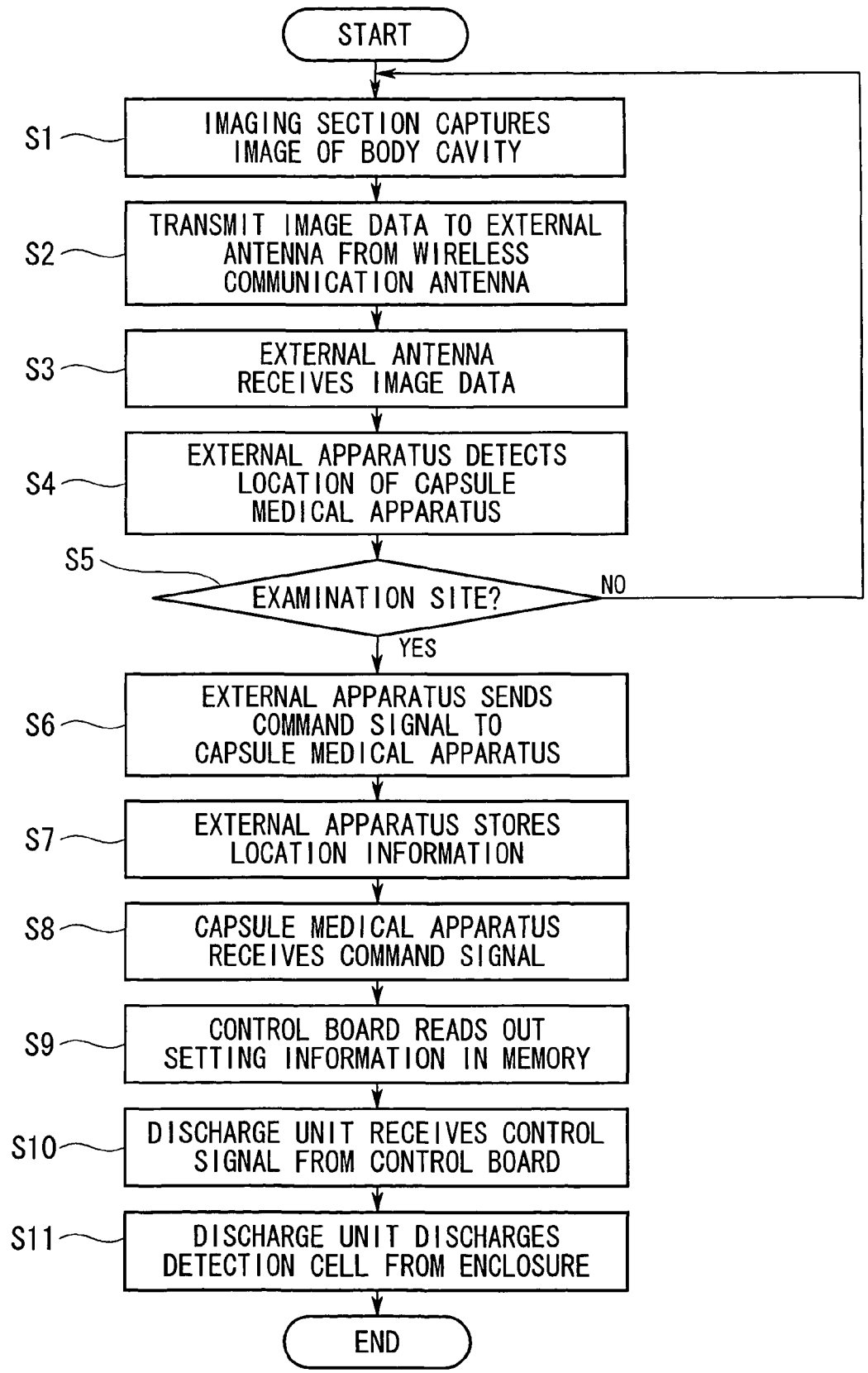
FIG. 18 is a flowchart applied when a capsule medical apparatus releases a detection cell.

The acquisition of in-vivo information of the patient 2 by the capsule medical apparatus system 10 of this embodiment, with the above-described structure, will now be described with reference to FIG. 18.

Before examination of the patient 2 is started, the technician or the operator turns ON the internal switch 32 of the capsule medical apparatus 3C. When the batteries 16 start supplying power to the components, the capsule medical apparatus 3C is inserted into the body cavity of the patient 2 per oral or per anal. While the capsule medical apparatus 3C advances in the body cavity, the imaging section 191 captures images of the body cavity with a control signal from the control board 14 to acquire image data (S1).

When the CMOS imager 198 of the imaging section 191 captures an image of the body cavity, the imaging board 199 sends the acquired image signal to the control board 14. The image signal is temporarily saved as image data in the memory 34 connected to the control board 14. When the external apparatus 6 issues at any desired time a command for transmitting image data to the capsule medical apparatus 3C, the control board 14 reads out the image data saved in the memory 34 and sends it to the wireless board 202. The image data sent to the wireless board 202 is transmitted to the external antenna 5 from the wireless communication antenna 192 (S2).

The transmitted image data is received by the external antenna 5 (S3), transferred to the external apparatus 6, and is then processed and saved in the PC 85. A determination circuit (first determining section), which is not shown in the figure, provided in the PC 85 compares the acquired image data with the set image in terms of brightness, color, frequency distribution, surface properties of a mucous membrane, etc. Alternatively, the external apparatus 6 measures the time elapsed since the capsule medical apparatus 3C has been inserted into the body cavity based on the number of frames of the image data. Based on this, the external apparatus 6 detects the location of the capsule medical apparatus 3C in the body cavity (S4) and determines whether it is at an examination site (S5).

If the external apparatus 6 determines that the capsule medical apparatus 3C has reached a preset examination site based on the location information, it issues a command signal for releasing a detection cell 4 to the capsule medical apparatus 3C (S6). At this time, the external apparatus 6 saves information about the location in which the detection cell 4 has been released (S7). When the capsule medical apparatus 3C receives the command signal (S8), the control board 14 reads out setting information about the release of the detection cells 4 from the memory 34 (S9). Thereafter, the release unit 13 receives a control signal including the setting information from the control board 14 (S10), and releases a predetermined number of detection cells 4 from the storage container 12 to the outside of the casing 11 (S11).

If the capsule medical apparatus 3C includes a plurality of detection cells 4, the above-described operation is repeated.

The detection cells 4 that have been released to examination sites in the body cavity detect blood (hemoglobin), tumor markers, protein, DNA, etc. included in a specimen such as a body fluid to acquire examination data. The detection cells 4 externally transmit the acquired examination data using electromagnetic waves, so that the in-vivo information in a plurality of sites in the body cavity can be acquired outside of the body.

As described above, according to the capsule medical apparatus system 10 of this embodiment, the capsule medical apparatus 3C stores a plurality of detection cells 4 and carries them into the body cavity. Thereby, a required number of detection cells 4 can be released according to the substances to be detected in the body cavity and the purpose of examination. Furthermore, since the capsule medical apparatus 3C includes the imaging section 191, image information about sites in the body cavity where detection cells 4 are released can be acquired.

In addition, since the location of the capsule medical apparatus 3C can be detected by the determination circuit provided in the external apparatus 6, the external apparatus 6 can control the release locations and the number of detection cells 4 released by the capsule medical apparatus 3C. Furthermore, the diagnosis capability can be enhanced by identifying the locations of lesions in combination with information about release locations of detection cells 4 and in-vivo information acquired by the detection cells 4.

This embodiment is not limited to the above-described structure.

First, the position-detecting section may be constructed so as to detect the location of the capsule medical apparatus 3C based on the electromagnetic field intensity transmitted from the capsule medical apparatus 3C.

Figure 19:
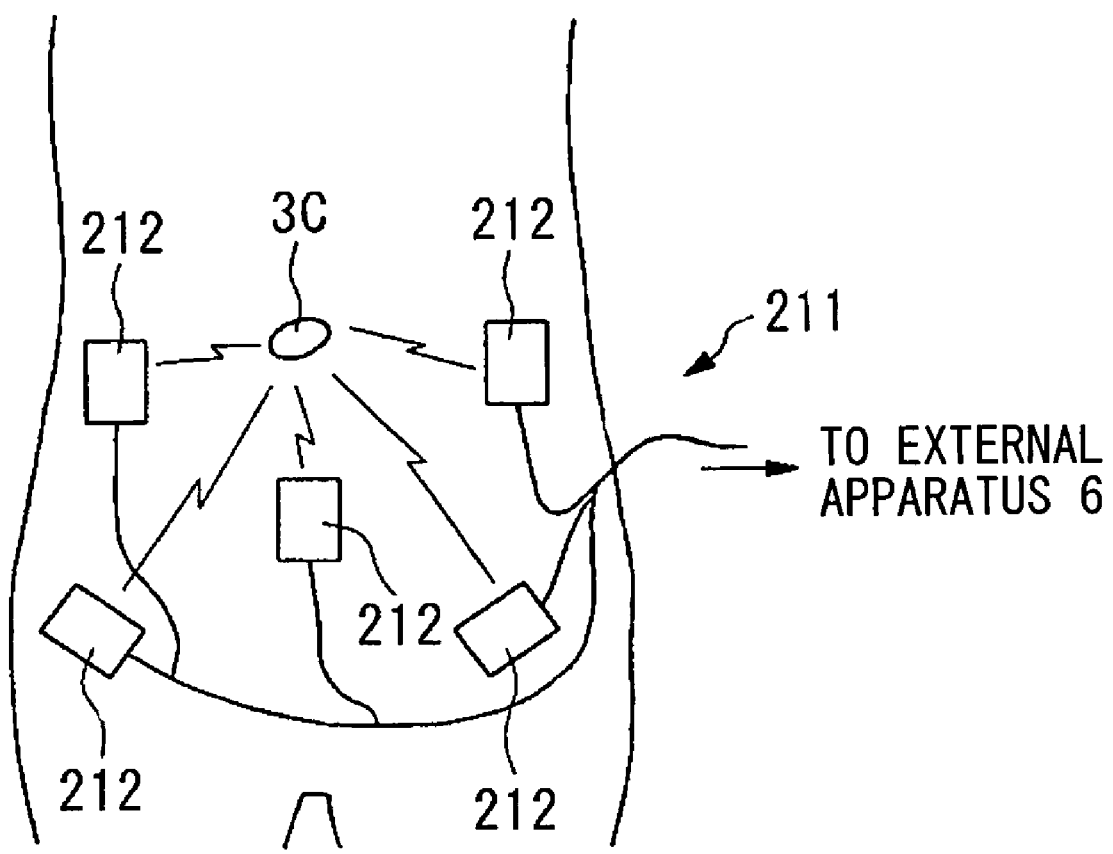
FIG. 19 is a diagram depicting a position-detecting section according to a first modification of the capsule medical apparatus system shown in FIG. 16.

More specifically, as shown in FIG. 19, a position-detecting section 211 may include the wireless communication antenna 192 of the capsule medical apparatus 3C, a plurality of receiving antennas 212 arranged outside the body, and a determination circuit (second determining section) provided in the PC 85. In this structure, each of the receiving antennas 212 measures the intensity of electromagnetic waves transmitted from the wireless communication antenna 192. Furthermore, the determination circuit of the PC 85 may detect the location of the capsule medical apparatus 3C based on the electromagnetic field intensity received with the receiving antennas 212.

It is preferable that the receiving antennas 212 be arranged near particular sites such as the stomach, intestine, and colon. Because of this, the above-described determination circuit can determine that the capsule medical apparatus 3C has reached the intestine when the electromagnetic field intensity received by the receiving antennas 212 positioned near the intestine exhibits the highest measurement. In this manner, the location of the capsule medical apparatus 3C can be detected reliably by the use of electromagnetic field intensity.

Second, the position-detecting section may be constructed so as to detect the location of the capsule medical apparatus 3C by the use of a magnetic field.

Figure 20:
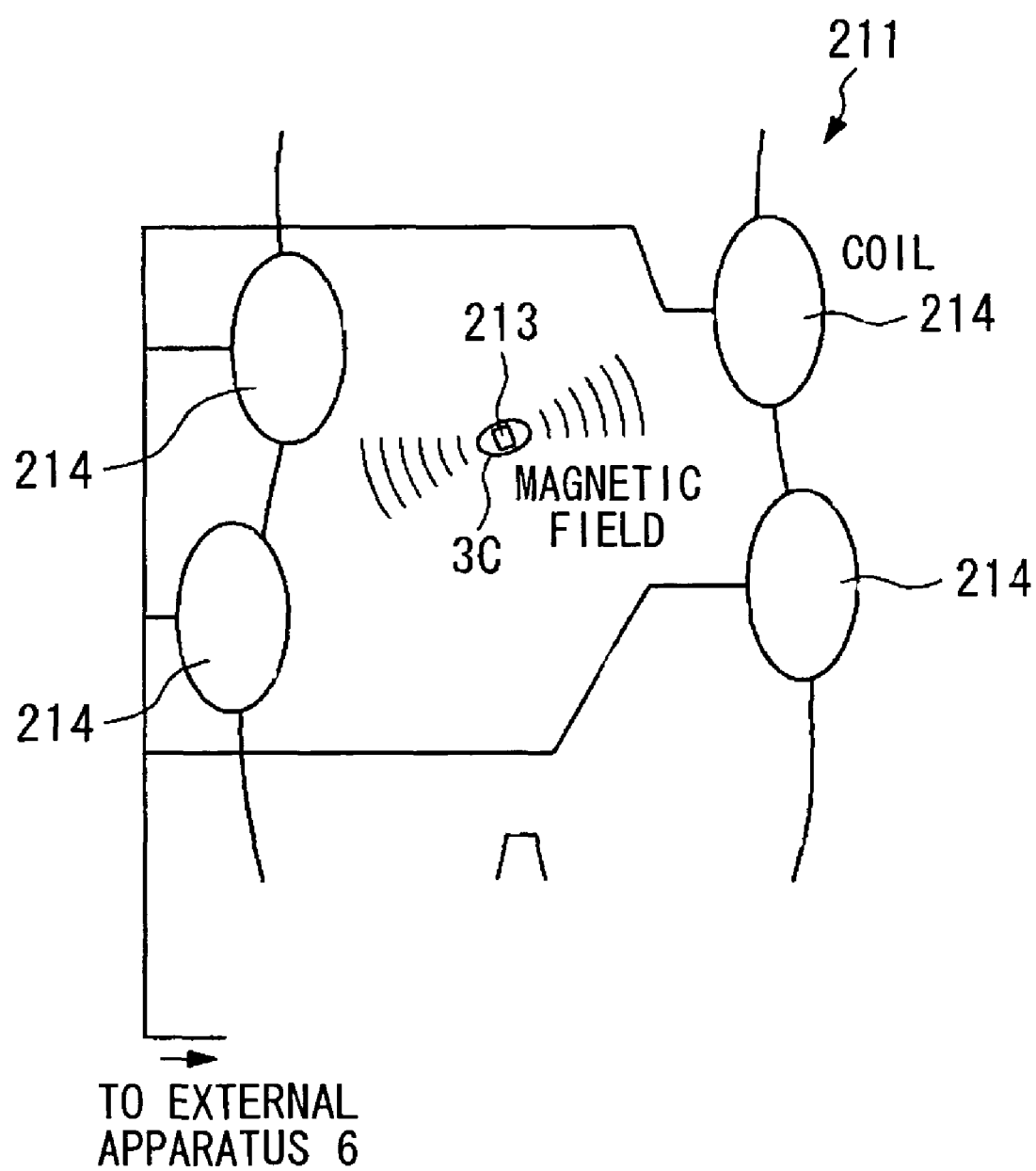
FIG. 20 is a diagram depicting a position-detecting section according to a second modification of the capsule medical apparatus system shown in FIG. 16.

More specifically, as shown in FIG. 20, the position-detecting section 211 may include a magnetic-field generating section 213 including a magnet, a coil, etc. (not shown) provided in the capsule medical apparatus 3C, a plurality of magnetic sensors 214 provided outside the body, and a determination circuit (third determining section) provided in the PC 85. In this structure, each of the magnetic sensors 214 is realized by, for example, an external coil (magnetic-field detecting unit), and measures the magnetic field vector generated by the magnetic-field generating section 213. Furthermore, the determination circuit of the PC 85 may detect the location of the capsule medical apparatus 3C based on the magnitude and direction of the magnetic field vector measured with the magnetic sensors 214.

In addition, in the position-detecting section 211, the magnetic-field generating section 213 may be a coil generating an AC magnetic field. In this case, position detection can be achieved by the use of the magnetic sensors 214 in a state where interference of, for example, physical quantities in the environment is less measurable as a result of the AC magnetic field being used. In this manner, the location of the capsule medical apparatus 3C can be detected reliably by the use of vector information of a magnetic field.

Third, the position-detecting section may be realized by, for example, a pH sensor (not shown in the figure) provided in the capsule medical apparatus 3C.

In this case, the capsule medical apparatus 3C determines whether the capsule medical apparatus 3C is located at the stomach, intestine, or colon based on the pH value in the body cavity detected by the pH sensor. This enables the position-detecting section to be constructed with a simple structure.

Fourth, in the capsule medical apparatus 3C, the position-detecting section may include the imaging section 191 and a position-detecting circuit (not shown in the figure) on the control board 14. The capsule medical apparatus 3C with this structure records in the memory 34 image data in the body cavity acquired by the imaging section 191 while moving in the body cavity to detect its own position with the position-detecting circuit on the control board 14. Therefore, since it is not necessary to use the external apparatus 6 while the capsule medical apparatus 3C releases a plurality of detection cells 4, the time for which the patient 2 is immobilized can be shortened.

The present invention is not limited to the above-described embodiments. Various modifications are conceivable within the scope of the present invention by, for example, partially combining the above-described embodiments. For example, in the first embodiment, an imaging device may be included and reagents or probes that specifically react with proteins, enzymes, and DNA may be used to examine these substances. In addition, in the second embodiment, blood component antibodies, tumor marker antibodies, etc. may be used to detect blood (hemoglobin), tumor markers, etc.

SCC, CYFRA, and other substances can be used as esophageal cancer markers and CEA, CA72-4, CA19-9, STN, and other substances can be used as gastric cancer markers. The present invention is not limited to these tumor markers, however. Substances such as AFP, CA125, NCC-ST-439, and DuPan-2 may also be used.

The invention claimed is:
1. An in-vivo information acquisition system comprising:
an in-vivo information acquisition apparatus to be inserted into a body to examine a specimen and acquire in-vivo information, the in-vivo information acquisition apparatus comprising:
a specimen-collecting section for collecting a specimen at an examination site in a body cavity;
a reactor section for reacting the specimen collected by the specimen-collecting section with a reagent;
a specimen-evaluating section for evaluating measurement data of the specimen reacted in the reactor section based on reference data and outputting an evaluation result;
a labeling section having identification information unique to the in-vivo information acquisition apparatus;
a memory for saving the evaluation result and the identification information unique to the in-vivo information acquisition apparatus;
a communication section for receiving a signal transmitted from outside and for transmitting to the outside the evaluation result output by the specimen-evaluating section;
a power supply section for supplying electrical power;
an indwelling section for affixing to a tissue surface in the body cavity; and
an external apparatus outside the body cavity, that acquires the evaluation result obtained by the in-vivo information acquisition apparatus via the communication section,
wherein a plurality of the in-vivo information acquisition apparatuses are provided inside the body cavity, in which collecting the specimen by the specimen-collecting section is simultaneously started in response to a first command signal sent from the external apparatus to the plurality of the in-vivo information acquisition apparatuses; and
the plurality of the in-vivo information acquisition apparatuses send the evaluation result and the identification information stored in the memory to the external apparatus in response to a second command signal sent from the external apparatus to the plurality of the in-vivo information acquisition apparatuses.

2. The in-vivo information acquisition apparatus according to claim 1, wherein the labeling section is a labeling tag for transmitting the identification information via wireless communication.

3. The in-vivo information acquisition apparatus according to claim 2, wherein the labeling tag is an RF-ID.

4. The in-vivo information acquisition apparatus according to claim 1, wherein the in-vivo information acquisition apparatus includes a power supply control section that controls the supply of power of the power supply section based on the signal received by the communication section.

5. The in-vivo information acquisition apparatus according to claim 1, wherein the in-vivo information acquisition apparatus includes an adhesive container for storing a biocompatible adhesive; and an adhesive release section for releasing the biocompatible adhesive.

6. The in-vivo information acquisition apparatus according to claim 1, wherein the power supply section is an externally chargeable power storage section that is supplied with electrical power by transmitting energy from outside the body wirelessly.

7. The in-vivo information acquisition apparatus according to claim 6, wherein the power storage section is an electrical double-layer capacitor.

8. The in-vivo information acquisition apparatus according to claim 1, wherein the in-vivo information acquisition apparatus includes
a cell enclosure having the specimen-evaluating section;
a shutter for closing the cell enclosure after the specimen is introduced to the interior of the cell enclosure; and
an ion-conducting actuator for controlling the opening and closing of the shutter.

9. The in-vivo information acquisition apparatus according to claim 1, wherein the specimen-evaluating section includes a photodetector for measuring an optical change of the specimen due to a reaction between the specimen and another substance.

10. The in-vivo information acquisition apparatus according to claim 9, wherein the specimen-evaluating section includes an illuminating element for emitting illuminating light onto the specimen.

11. The in-vivo information acquisition apparatus according to claim 10, wherein the illuminating element is a wavelength tunable light source.

12. The in-vivo information acquisition apparatus according to claim 9, wherein the specimen-evaluating section functions as a blood sensor for detecting the presence of blood.

13. The in-vivo information acquisition apparatus according to claim 9, wherein the specimen-evaluating section functions as a protein sensor for detecting a particular protein.

14. The in-vivo information acquisition apparatus according to claim 9, wherein the specimen-evaluating section functions as an enzyme sensor for detecting a particular enzyme.

15. The in-vivo information acquisition apparatus according to claim 9, wherein the specimen-evaluating section functions as a gene sensor for detecting a particular gene.

16. The in-vivo information acquisition apparatus according to claim 1, wherein the in-vivo information acquisition apparatus includes an imaging section for acquiring an image of the body cavity.

17. The in-vivo information acquisition apparatus according to claim 1,
wherein the specimen-evaluating section includes an arithmetic section for operating an arithmetic operation, and
wherein the measurement data and the reference data are subjected to the arithmetic operation in the arithmetic section so as to calculate examination data.

18. An in-vivo information acquisition system comprising:
an in-vivo information acquisition apparatus to be inserted into a body to examine a specimen and acquire in-vivo information, the in-vivo information acquisition apparatus comprising:
a specimen-collecting section for collecting a specimen at an examination site in a body cavity;
a reactor section for reacting the specimen collected by the specimen-collecting section with a reagent;
a specimen-evaluating section for evaluating measurement data of the specimen reacted in the reactor section on the basis of reference data and outputting an evaluation result;
a labeling section having identification information unique to the in-vivo information acquisition apparatus;
a memory for saving the evaluation result and the identification information unique to the in-vivo information acquisition apparatus;

a communication section for receiving a signal transmitted from outside and for transmitting to the outside the evaluation result by the specimen-evaluating section; and
a power supply section for supplying electrical power,
an indwelling section for affixing to a tissue surface in the body cavity;
an external apparatus, arranged outside the body cavity, that acquires the evaluation result obtained by the in-vivo information acquisition apparatus via the communication section,
wherein a plurality of the in-vivo information acquisition apparatuses are provided inside the body cavity, in which collecting the specimen by the specimen-collecting section is simultaneously started in response to a first command signal sent from the external apparatus to the plurality of in-vivo information acquisition apparatuses,
wherein the plurality of the in-vivo information acquisition apparatuses send only the identification information stored in the memory to the external apparatus in response to a second command signal sent from the external apparatus to the plurality of in-vivo information acquisition apparatuses,
wherein the external apparatus sequentially sends an individual third command signal to each of the in-vivo information acquisition apparatuses after identifying each of the identification information unique to the in-vivo information acquisition apparatus sent, and
wherein each of the in-vivo information acquisition apparatuses sequentially sends the evaluation result stored in the memory to the external apparatus in response to the third command signal.

\* \* \* \* \*